(12) United States Patent
I-Hung

(10) Patent No.: US 10,543,243 B2
(45) Date of Patent: Jan. 28, 2020

(54) SOYBEAM SEED EXTRACT, METHOD FOR PRODUCING THE SAME AND USES THEREOF

(71) Applicant: CHARSIRE BIOTECHNOLOGY CORP., Tainan (TW)

(72) Inventor: Chu I-Hung, Tainan (TW)

(73) Assignee: CHARSIRE BIOTECHNOLOGY CORP., Tainan (TW)

(*) Notice: Subject to any disclaimer, the term of this patent is extended or adjusted under 35 U.S.C. 154(b) by 493 days.

(21) Appl. No.: 15/174,266

(22) Filed: Jun. 6, 2016

(65) Prior Publication Data
US 2017/0348370 A1    Dec. 7, 2017

(51) Int. Cl.
*A61K 36/48*    (2006.01)
*A61K 36/00*    (2006.01)

(52) U.S. Cl.
CPC ........ *A61K 36/48* (2013.01); *A61K 2236/331* (2013.01); *A61K 2236/333* (2013.01); *A61K 2236/53* (2013.01)

(58) Field of Classification Search
None
See application file for complete search history.

(56) References Cited

U.S. PATENT DOCUMENTS

| | | |
|---|---|---|
| 7,112,344 B2 | 9/2006 | Chu |
| 7,282,226 B2 | 10/2007 | Chu |
| 2002/0009509 A1 | 1/2002 | Bombardelli |
| 2004/0253647 A1* | 12/2004 | Mathews ........... G01N 33/5008 435/7.2 |
| 2005/0112219 A1 | 5/2005 | Chu |
| 2006/0147397 A1 | 7/2006 | Uehara et al. |

FOREIGN PATENT DOCUMENTS

| | | |
|---|---|---|
| CA | 2 652 826 A1 | 10/2007 |
| CN | 1507904 A | 6/2004 |
| CN | 1608632 A | 4/2005 |
| CN | 102397317 A | 4/2012 |
| CN | 103356940 A | 10/2013 |
| CN | 104546998 A * | 4/2015 |
| JP | 4-139132 | 5/1992 |
| JP | 2001-097842 A | 4/2001 |
| JP | 2003-252777 A | 9/2003 |
| JP | 2008-308505 A | 12/2008 |
| JP | 2009-132651 A | 6/2009 |
| JP | 2010-59142 A | 3/2010 |
| JP | 4681218 B2 | 2/2011 |
| JP | 2012-180340 A | 9/2012 |
| JP | 2012180340 A * | 9/2012 |
| JP | 2012-219014 A | 11/2012 |
| JP | 2012_219014 A | 11/2012 |
| JP | 2015-51970 A | 3/2015 |
| JP | 2015-051970 A | 3/2015 |
| JP | 2016-79124 A | 5/2016 |
| KR | 10-1284071 B | 7/2013 |
| WO | 99/06057 A1 | 2/1999 |
| WO | 2012/017435 A2 | 2/2012 |

OTHER PUBLICATIONS

Vickers (A Vaccine Against Alzheimer's Disease, Drug Aging 2002 vol. 19, No. 2 pp. 487-494).*
Search Report.
Written Opinion.
JP 2012-219014 A_Machine Translation.
CN 102397317 A_Machine Translation.
JP 2015-051970 A_Machine Translation.
CN 1507904 A_Machine Translation.
Office Action dated Nov. 23, 2016 for European Application No. 16173129.4.
Office Action dated Nov. 24, 2016 for Australian Application No. 2016203746.
English translation of JP 2012-219014 A.
English abstract of JP 2015-51970 A.
English abstract of CN 103356940 A.
Canadian Office Action dated Oct. 31, 2017 for Canadian Application No. 2,932,277.
Non-English Russian Office Action dated Nov. 1, 2017 with English translation for Russian Application No. 2016122238.
Non-English Korean Office Action dated Dec. 19, 2017 with English summary for Korean Application No. 10-2016-0070442.
Luthria, D. L., et al., "Comparison of extraction solvents and techniques used for the assay of isoflavones from soybean", Food Chemistry, vol. 105, 2007, pp. 325-333.
Sinha, L. K., et al., "Effect of operating parameters on mechanical expression of solvent-soaked soybean-grits", J. Food Sci. Technol., vol. 52, No. 5, May 2015, pp. 2942-2949.
Jeong, J. H., et al., "Black Soybean Extract Protects Against TMT-Induced Cognitive Defects in Mice", J. Med. Food, vol. 17, No. 1, 2014, pp. 83-91.
Non-English Japanese Office Action dated Jul. 4, 2017 with English summary for Japanese Application No. 2016-112646.
Non-English Korean Office Action dated Aug. 18, 2017 with English summary for Korean Application No. 10-2017-0069248.
Non-English Korean Office Action dated Aug. 18, 2017 with English summary for Korean Application No. 10-2017-0069249.
Non-English Korean Office Action dated Aug. 18, 2017 with English summary for Korean Application No. 10-2017-0069250.
English abstract of JP 2016-79124 A.
English abstract of JP 2010-59142 A.
English abstract of JP 2009-132651 A.
English abstract of JP 2003-252777 A.
English abstract of JP 2008-308505 A.
English abstract of JP 2012-180340 A.

(Continued)

*Primary Examiner* — Michael Barker
(74) *Attorney, Agent, or Firm* — Ladas & Parry LLP

(57) ABSTRACT

The invention relates to a soybean seed extract, method for producing the same and uses of the extract of soybean seeds in promoting wound healing, promoting neuron cell proliferation and/or treating brain diseases and/or neurodegenerative diseases, treating breast cancer, reducing side effects of interfering with DNA and/or RNA replication drugs and/or enhancing pharmaceutical effects of interfering with DNA and/or RNA replication drugs.

9 Claims, 14 Drawing Sheets

(56) References Cited

OTHER PUBLICATIONS

Odani, S., et al., "Soybean hydrophobic protein Isolation, partial characterization and the complete primary structure", Eur. J. Biochem., vol. 162, 1987, pp. 485-491.
Johansen, H. N., et al., "Influence of Extraction Solvent and Temperature on the Quantitative Determination of Oligosaccharides from Plant Materials by High-Performance Liquid Chromatography", J. Agric. Food Chem., vol. 44, 1996, pp. 1470-1474.
Park, N. H., et al., "Soybean extract showed modulation of retinoic acid-related gene expression of skin and photo-protective effects in keratinocytes", International Journal of Cosmetic Science, 2012, pp. 1-7.
Bhuiyan, M. I. H., et al., "Anthocyanins Extracted from Black Soybean Seed Coat Protect Primary Cortical Neurons against in Vitro Ischemia", Biol. Pharm. Bull., vol. 35, No. 7, Jul. 2012, pp. 999-1008.
Sung, Mi-Kyung, et al., "Cytotoxic and Apoptotic Effects of Soybean and Brown Rice Extracts on Hormone Dependent/Independent Breast Cancer Cell Lines", J. Korean Soc. Food Sci. Nutr., vol. 31, No. 3, 2002, pp. 521-526.
Non-English Office Action dated Mar. 2, 2017 for Korean Application No. 10-2016-0070442 with English translation.
Non-English Office Action and Search Report dated Mar. 6, 2017 for Taiwan Application No. 102129406 with English translation of the Search Report.
English abstract of CN 1608632 A.
van Ee, J. H., "Soy constituents: modes of action in low-density lipoprotein management", Nutrition Reviews, vol. 37, No. 4, pp. 222-229.
Kerr, G., "What Are the Benefits of Soy Lecithin Granules?", Livestrong.com, Mar. 13, 2014 with English translation.
Dixit, A. K., et al., "Soybean constituents and their functional benefits", Opportunity, Challenge and Scope of Natural Products in Medicinal Chemistry, 2011, pp. 367-380.
Saeidnia, S., et al., "The Story of Beta-sitosterol—A Review", European Journal of Medicinal Plants, vol. 4, No. 5, 2014, pp. 590-609.
Berger, A., et al., "Plant sterols: factors affecting their efficacy and safety as functional food ingredients", Lipids in Health and Disease, vol. 3, 2004, pp. 1-16.
"Can phosphatidylserine improve memory?", Jun. 16, 2009 with English translation.
Examination Report issued in corresponding Canada Patent Application No. 2,932,277 (references cited therein were previously submitted in an IDS and therefore are not cited in this IDS).
Search and Examination Reports issued in corresponding Malaysia Patent Application No. PI 2016702064 (references cited therein were previously submitted in an IDS and therefore are not cited in this IDS).
Written Opinion issued in corresponding Singapore Patent Application No. 10201604572Q (with the exception of the Chinese patent reference cited herein, the other references cited the Written Opinion were previously submitted in an IDS and therefore are not cited in this IDS).
Machine English translation of Chinese patent reference CN1507904.
Adlercreutz, H.; Phyto-oestrogens and cancer. The Lancet Oncology, 2002. vol. 3, p. 364-373.
Lee-Jane W. Lu, Karl E. Anderson, James J. Grady, and Manubai Nagamani ; Effects of Soya Consumption for one Month on Steroid Hormones in Premenopausal Women: Implications for Breast Cancer Risk Reduction. Cancer Epidemiol Biomarkers Prev. Jan. 1996; 5(1): 6370.
Matvienko, O. A., Lewis, D. S., Swanson, M., Aendt, B., Rainwater, D. L., Stewart, J., and Alekel, D. L.; A Single Daily Dose of Soybean Phytosterols in Ground Beef Decreases Serum Total Cholesterol and LDL Cholesterol in Young, Mildly Hypercholesterolemic Men. Am J Clin Nutr., 2002, 76, p. 57-64.
Takahata, Y., O.-Kameyama, M., Furuta, S., Takahashi, M., and Suda, I.; Highly Polymerized Procyanidins in Brown Soybean Seed Coat with a High Radical-Scavenging Activity. J. Agric. Food Chem., 2001, 49, p. 5843-5847.
Minamiyama, Y., Yoshikawa, T., Tanigawa, T., Takahashi, S., Naito, Y., Ichikawa, H., and Kondo, M.; Antioxidative Effects of a Processed Grain Food. J. Nutr. Sci. Vitaminol., 1994, 40, p. 467-477.
Wu, S.-J., Wang, J.-S. and Chang, C.-H.; Evaluation of Hepatoprotective Activity of Legumes. Phytomedicine, 2001, vol. 8(3), p. 213-219.

* cited by examiner

AlCl₃

● bait

AlCl₃+Ceam base

AlCl₃+N2

Sham

2VO

● bait

M

M1

M3

SOYBEAM SEED EXTRACT, METHOD FOR PRODUCING THE SAME AND USES THEREOF

FIELD OF THE INVENTION

The invention relates to a soybean seeds extract, method for producing the same and uses of the soybean seed extract in promoting wound healing, promoting neuron cell proliferation and/or treating brain diseases and/or neurodegenerative diseases, treating breast cancer, reducing side effects of interfering with DNA and/or RNA replication drugs, and/or enhancing pharmaceutical effects of interfering with DNA and/or RNA replication drugs.

BACKGROUND OF THE INVENTION

*Glycine max* (L.) Merr., including soybean and black soybean, is one of the most important sources of oil and proteins in the world. For instance, soybeans can be processed to obtain edible oil that is used as salad oil, or for manufacture of margarine and shortening. Soybean oil can be also used in the manufacture of paints, linoleum, oilcloth, printing inks, soaps, insecticides, and disinfectants. Besides, lecithin phospholipids obtained from the by-products of the oil industry, can be used as wetting and stabilizing agents in food, cosmetics, pharmaceuticals, leathers, paints, plastics, soaps, and detergents. Soy meal is a very protein-rich feeding stuff for livestock. In addition, soybean protein can be used in manufacture of synthetic fibers, adhesives, textile sizing, waterproofing, fire-fighting foams and so on.

In medical use, soybeans have been reported to have effects on many diseases.

Soybean can be used as a nutritious supplement for regulating the functions of bowels, heart, kidney, liver, and stomach. Since soybean oil contains a high amount of unsaturated fatty acids, it can be used to combat hypercholesteremia. Medical lecithin from soybeans functions as a lipotropic agent. In addition, tigmasterol known as an anti-stiffness factor, and sitosterol used as a replacement for diosgenin in some antihypertensive drugs, are prepared from soybeans. Isoflavones and phyto-oesterogens found in soybeans have been suggested to have a preventive effect against various cancers comprising breast, prostate, and colon cancers (Adlercreutz, H.; Phyto-oestrogens and cancer. The Lancet Oncology, 2002, Vol. 3, p. 364-373). Other literature indicates that in order to achieve the effect on preventing the occurrence of breast cancer of isoflavones, at least 100 mg daily dose should be consumed continually for a month, and it represents that only by being consumed continually at the high dose, isoflavones exhibit anti-cancer effect (Lu L J, Anderson K E, Grady J J, Nagamani M.; Effects of soya consumption for one month on steroid hormones in premenopausal women: implications for breast cancer risk reduction. Cancer Epidemiol Biomarkers Prev. 1996 January; 5(1): 6370). Consumption of phytosterol-supplemented margarine is also found to lower total plasma cholesterol and LDL-cholesterol concentrations in older middle-aged hypercholesterolemic individuals (Matvienko, O. A., Lewis, D. S., Swanson, M., Aendt, B., Rainwater, D. L., Stewart, J., and Alekel, D. L.; A single daily dose of soybean phytosterols in ground beef decreases serum total cholesterol and LDL cholesterol in young, mildly hypercholesterolemic men. Am J Clin Nutr., 2002, 76, p. 57 64).

Some extracts from soybean have been also reported to have pharmaceutical effects. 1,1-diphenyl-2-picrylhydrazyl (DPPH) radical-scavenging activity of 70% aqueous acetone extract from the seed coat of a brown soybean variety, Akita-Zairai, is disclosed (Takahata, Y., O.-Kameyama, M., Furuta, S., Takahashi, M., and Suda, 1.; Highly polymerized procyanidins in brown soybean seed coat with a high radical-scavenging activity. J. Agric. Food Chem., 2001, 49, p. 5843 5847). An extract from germ extracts, soybean, rice bran, tear grass, sesame, wheat, citron, green tea, green leaf extract, and malted rice, which are slowly roasted under a temperature at less than 60° C. and fermented with *Aspergillus oryzae* over 3 days to transform each ingredient into low molecular weight substances, is found to have antioxidative effects (Minamiyama, Y., Yoshikawa, T., Tanigawa, T., Takahashi, S., Naito, Y., Ichikawa, H., and Kondo, M.; Antioxidative effects of a processed grain food. J. Nutr. Sci. Vitaminol., 1994, 40, p. 467 477). Water extract of black soybean is also reported to effect on acetaminophen-induced liver injury by measuring serum glutamate-oxalate-transaminase (sGOT) and serum glutamate-pyruvate-transaminase (sGPT) activities in rats (Wu, S.-J., Wang, J.-S. and Chang, C.-H.; Evaluation of hepatoprotective activity of legumes. Phytomedicine, 2001, Vol. 8(3), p. 213 219).

Some specific extracts from soybean have been found to be applied in cosmetics or pharmaceuticals in treating some skin diseases. A soya extract, which contains sphingomyelins and phospholipids in defined ratios is disclosed to be used in cosmetics for the treatment of dry skin (U.S. Patent Pub. No. US2002/0009509 A1). Such extract is produced by extracting ripe whole soya beans or oil-free soya flour using aliphatic alcohols alone or in a mixture with water and followed by the treatment with aliphatic hydrocarbons and with aliphatic ketones. Therefore, the extract is liposoluble.

An acne medicine, cosmetic production inhibitor or cosmetic composition containing one or more plant extracts selected from whey, and a *Phellodendeon amurense* Ruprecht extract, and further one or more extracts selected from *Scutellaria baicalensis* Geoegi, *Symphytum officinale* Linne, and *Glycine max* (L.) Merrill, is found to be effective on preventing or treating skin diseases such as acne or inflammatory chapped skin caused by the acne (JP Patent No. 2001097842).

Products of fermenting soybean by microorganisms are also applied as anti-active oxygen action compositions, agents, foods, cosmetics and medicines (such as JP Patent No. 4139132).

Although many uses of soybeans have been reported, different applications of soybean extract are yet to be developed.

SUMMARY OF THE INVENTION

The invention relates to a soybean seed extract, method for producing the same and uses of the soybean seed extract in promoting wound healing, promoting neuron cell proliferation and/or treating brain diseases and/or neurodegenerative diseases, treating breast cancer, reducing side effects of interfering with DNA and/or RNA replication drugs, and/or enhancing pharmaceutical effects of interfering with DNA and/or RNA replication drugs.

The invention is to provide an extract composition comprising a soybean seed extract, which soybean seed extract is prepared by a process comprising steps of:
  (a) providing soybean seeds and an extracting solution, which extracting solution is water or an alcohol solution containing alcohol at the concentration lower than about 90 wt %;
  (b) extracting the soybean seeds with the extracting solution at a barometric pressure lower than about 1 atm and at a temperature lower than about 60° C. to obtain an crude extract; and (c) removing solids from the crude extract to obtain a liquid portion.

The present invention is also to provide a method for preparing the extract composition as mentioned above comprising a process for preparing the soybean seed extract comprising steps of:

(a) providing soybean seeds and an extracting solution, which extracting solution is water or an alcohol solution containing alcohol at the concentration lower than about 90 wt %;

(b) extracting the soybean seeds with the extracting solution at a barometric pressure lower than about 1 atm and at a temperature lower than about 60° C. to obtain an crude extract; and (c) removing solids from the crude extract to obtain a liquid portion.

The present invention is also to provide use of the extract composition as mentioned above in the manufacture of a medicament of promoting wound healing.

The present invention is also to provide a method for promoting wound healing in a subject in need of such promotion comprising administering to said subject an effective amount of the extract composition as mentioned above.

The present invention is also to provide use of the extract composition as mentioned above in the manufacture of a medicament of promoting neuron cell proliferation and/or treating brain diseases and/or neurodegenerative diseases.

The present invention is also to provide a method for promoting neuron cell proliferation and/or treating brain diseases and/or neurodegenerative diseases in a subject in need of such promotion and/or treatment comprising administering to said subject an effective amount of the extract composition as mentioned above.

The present invention is also to provide use of the extract composition as mentioned above in the manufacture of a medicament of treating breast cancer.

The present invention is also to provide a method for treating breast cancer in a subject in need of such treatment comprising administering to said subject an effective amount of the extract composition as mentioned above.

The present invention is also to provide use of the extract composition as mentioned above in the manufacture of a medicament of reducing side effects of interfering with DNA and/or RNA replication drugs and/or enhancing pharmaceutical effects of interfering with DNA and/or RNA replication drugs.

The present invention is also to provide a method for reducing side effects of interfering with DNA and/or RNA replication drugs and/or enhancing pharmaceutical effects of interfering with DNA and/or RNA replication drugs in a subject in need of such reduction and/or enhancement comprising administering to said subject an effective amount of the extract composition as mentioned above.

The present invention is described in detail in the following sections. Other characteristics, purposes and advantages of the present invention can be found in the detailed description and claims.

BRIEF DESCRIPTION OF THE DRAWINGS

As shown in FIG. 11, the GMA1 was combined with GMC1 at different concentrations: 0.009%, 0.045% and 0.09%, respectively. For comparison, two groups treated with cream base and CGS-21680 were also conducted in all experimental studies. The results show that for wound healing, the combination effects of the dose levels, 0.009%, 0.045% and 0.09%, of GMA1 with GMC1 are better than GMC1 alone. The most effective combination treatment is found in the highest dosage of GMA1 (0.09%).

CT grade of brain injury:
0: No obvious abnormality on CT scans
1: Small area of abnormal density region in brain tissue
2: Abnormal density regions in over 25% of unilateral brain tissue, or small area of abnormal density regions in bilateral brain tissue
3: Abnormal density regions in over 50% of unilateral brain tissue, midline shift, or abnormal density regions in over 25% of bilateral brain tissue
4: Abnormal density regions in over 50% of bilateral brain tissue, or apparent midline shift/distortion.

Figure 25:
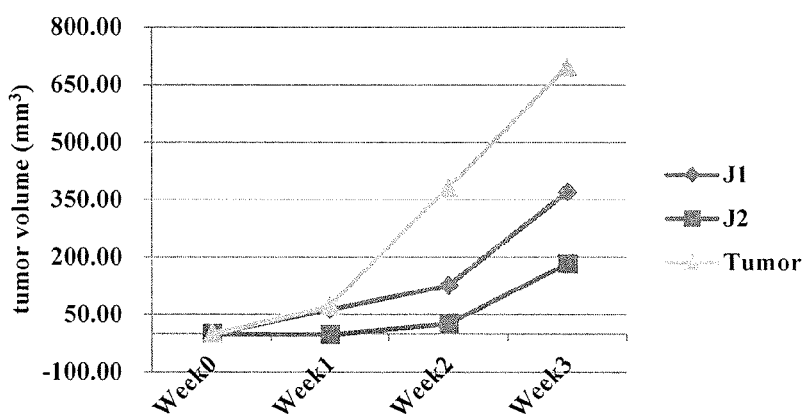

FIG. 25 shows the diagram of the tumor growth rate of the nude mice. The tumor was induced in the nude mice and the mice were subjected to grouping and administrated with the extract composition on the tumor area and the whole back skin with the dosage of 0.1 g/day when the tumor grew to a determined volume. The results show that the extract composition can decrease the tumor growth rate compared to the tumor control group.

Figure 26:
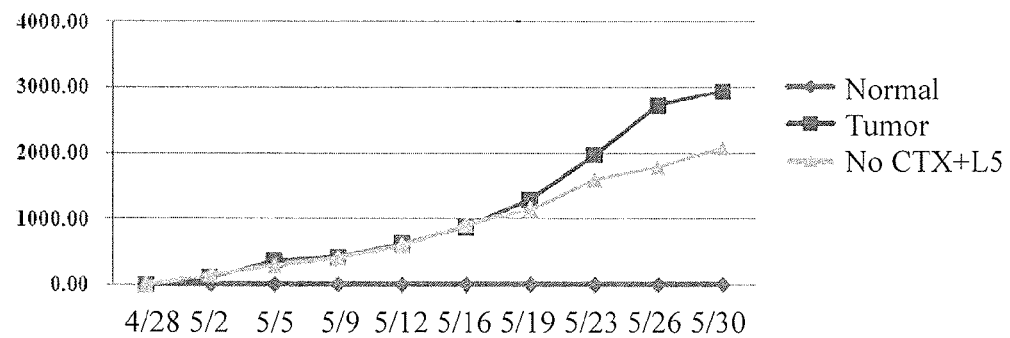

FIG. 26 shows the diagram of the tumor growth rate of the nude mice. The tumor was induced in the nude mice and the mice were subjected to grouping and administrated with GMC1 and GMA1 on the tumor area and the whole back skin with the dosage of 0.1 g/day when the tumor grew to a determined volume. The results show that the extract composition can decrease the tumor growth rate compared to the tumor control group.

Figure 27:
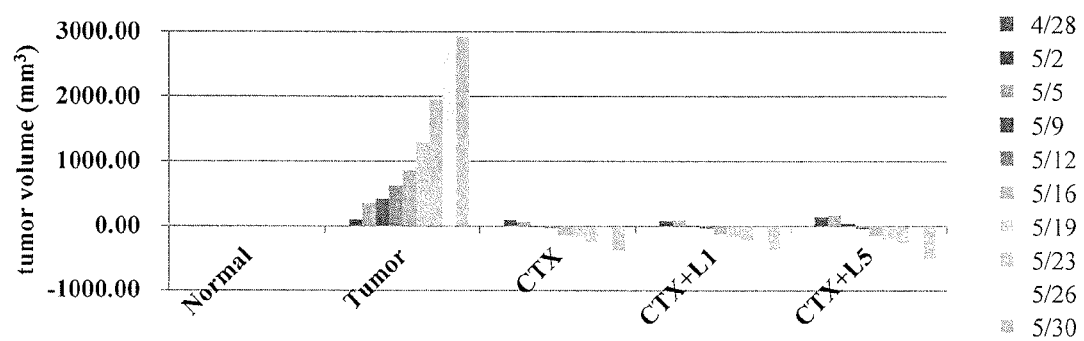

FIG. 27 shows the diagram of the tumor growth rate of the nude mice. The tumor was induced in the nude mice and the mice were subjected to grouping and administrated with CTX injection and GMC1 and GMA1 on the tumor area and the whole back skin with the dosage of 0.1 g/day when the tumor grew to a determined volume. The results show that the extract composition can decrease the tumor growth rate compared to the CTX control group.

DETAILED DESCRIPTION OF THE INVENTION

The invention is to provide an extract composition comprising a soybean seed extract, which soybean seed extract is prepared by a process comprising steps of:

(a) providing soybean seeds and an extracting solution, which extracting solution is water or an alcohol solution containing alcohol at the concentration lower than about 90 wt %;
(b) extracting the soybean seeds with the extracting solution at a barometric pressure lower than about 1 atm and at a temperature lower than about 60° C. to obtain an crude extract; and
(c) removing solids from the crude extract to obtain a liquid portion.

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the extract of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder, disease or condition to which such term applies, or one or more symptoms of such disorder, disease or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The extract composition according to the invention comprises the soybean seed extract. According to the present invention, depending on the test a color of the seeds, the soybean may be referred to yellow soybean, vegetable soybean, white soybean, peel beans, green bean, black soybean; preferably yellow soybean or black soybean. The soybean according to the invention belongs to Fabaceae family, *Glycine* genus; preferably, the soybean is *Glycine max* (L.) Merrill, *Glycine formosana* Hosokawa or *Glycine soja* auct. non Sieb. & Zucc.

The soybean seed according to the invention preferably refers to the seed obtained by removing a shell from a pod. Generally, a soybean fruit is the pod with hair, and the shell of the pod covers the seeds. The shell of the pod is very hard and waterproof for protecting the seeds inside. The manner of obtaining the soybean seeds from the soybean fruit, i.e. removing the shell of the pod, is known by artisans skilled in this field. Preferably, the soybean seed according to the invention comprises seed coat, cotyledon and hypocotyl.

The soybean seed extract according to the invention is prepared by a process comprising steps of:
(a) providing soybean seeds and an extracting solution, which extracting solution is water or an alcohol solution containing alcohol at the concentration lower than about 90 wt %;

(b) extracting the soybean seeds with the extracting solution at a barometric pressure lower than about 1 atm and at a temperature lower than about 60° C. to obtain an crude extract; and (c) removing solids from the crude extract to obtain a liquid portion.

The extracting solution for extracting the soybean seeds according to the invention is water or an alcohol solution containing alcohol at the concentration lower than about 90 wt %. Preferably, the alcohol is C1 to C7 alcohol. The term "C1 to C7 alcohol" as used herein refers to linear or branched, substituted or unsubstituted, mono- or poly- functional, and saturated or unsaturated alcohol; preferably unsubstituted, mono-functional and saturated alcohol. In one preferred embodiment of the invention, the C1 to C7 alcohol is selected from the group consisting of methanol, ethanol, n-propanol, isopropanol, n-butanol, iso-butanol, sec-butanol, tert-butanol, 1-pentanol, 2-pentanol, 3-pentanol, 2-methyl-1-butanol, 2-methyl-2-butanol, 3-methyl-2-butanol, 3-methyl-1-butanol, 2,2-dimethyl-1-propanol, 1-hexanol, 2,4-hexadiene-1-ol, 2-methyl-cyclopentanol, cyclohexanol, 1-heptanol, 2-heptanol, or cycloheptyl alcohol. More preferably, the C1 to C7 alcohol is methanol or ethanol; most preferably, the C1 to C7 alcohol is ethanol. The C1 to C7 alcohol can be used solely or in combinations.

The alcohol as used herein is preferably an alcohol solution with a concentration lower than about 90% (v/v); preferably from about 5% (v/v) to about 90% (v/v); more preferably from about 30% (v/v) to about 85% (v/v); still more preferably from about 50% (v/v) to about 75% (v/v).

The process according to the invention comprises (b) extracting the soybean seeds with the extracting solution at a barometric pressure lower than about 1 atm and at a temperature lower than about 60° C. to obtain an crude extract. The manner of extracting a part of a seed with a solution is well-known to artisans skilled in this field. For example, the crude extract can be obtained by dividing the soybean seeds into pieces in any manner such as grinding, stirring, disturbing, cutting or shredding, and soaking the pieces in the extracting solution for extraction. The manners for dividing the seeds in the field are able to be applied in the invention. In one preferred embodiment of the invention, the soybean seeds are grinded into powder. In one preferred embodiment of the invention, the soybean seeds are soaked in the extracting solution for extraction; more preferably, the soybean seeds are soaked in the extracting solution and subjected to ultrasonic vibration extraction.

According to the process of the invention, prior to step (b), the soybean seeds are preferably dried.

According to the invention, the ratio (w/v) of the soybean seeds and the extracting solution is not specifically restricted. In one preferred embodiment of the invention, the ratio (w/v) of the soybean seeds and the extracting solution is about 1:1 to about 1:30; more preferably about 1:5 to about 1:20; and most preferably about 1:10.

The temperature of extraction in the step (b) according to the invention is lower than about 60° C.; preferably from about 25° C. to about 55° C.; more preferably from about 30° C. to about 50° C.; still more preferably about 45° C.

In one preferred embodiment of the invention, the extraction step (b) can be repeated, and the extract is collected by merging.

The process according to the invention comprises the step (c) removing solids from the crude extract to obtain a liquid portion. The manner of removing the solids to obtain the liquid fraction is well-known to artisans skilled in this field, and examples include but not limited to filtration, centrifugation, or precipitation.

Preferably, the process according to the invention further comprises a step (d) of concentrating the liquid portion obtained in the step (c) to obtain a concentrated solid portion. The manner of concentrating is well-known to artisans skilled in this field, such as by a reduced-pressure condenser.

Preferably, the process for according to the invention further comprises a step (e) of drying the concentrated solid portion obtained in the step (d). The manner of drying is well-known to artisans skilled in this field, such as air-drying or by a freeze drier.

In one preferred embodiment of the invention, the soybean seed extract is subjected to an ion chromatography assay with CarboPac PA1 Analytical (4×250 mm) column. The mobile phase is 87% water and 13% 500 mM NaOH; the internal standard is maltose monohydrate. The isocratic elution is applied with the low rate of 1.0 ml/min and the cycle of 0.5 second. In every cycle, the assay is conducted with the relative potential of 0.1 V at 0.00 second to 0.2 second; 0.1 V at 0.2 second to 0.4 second; −2.0 V at 0.41 second to 0.42 second; 0.6 V at 0.43 second; −0.1 V at 0.44 second to 0.5 second, and the total assay duration is 55 minutes.

Figure 1:
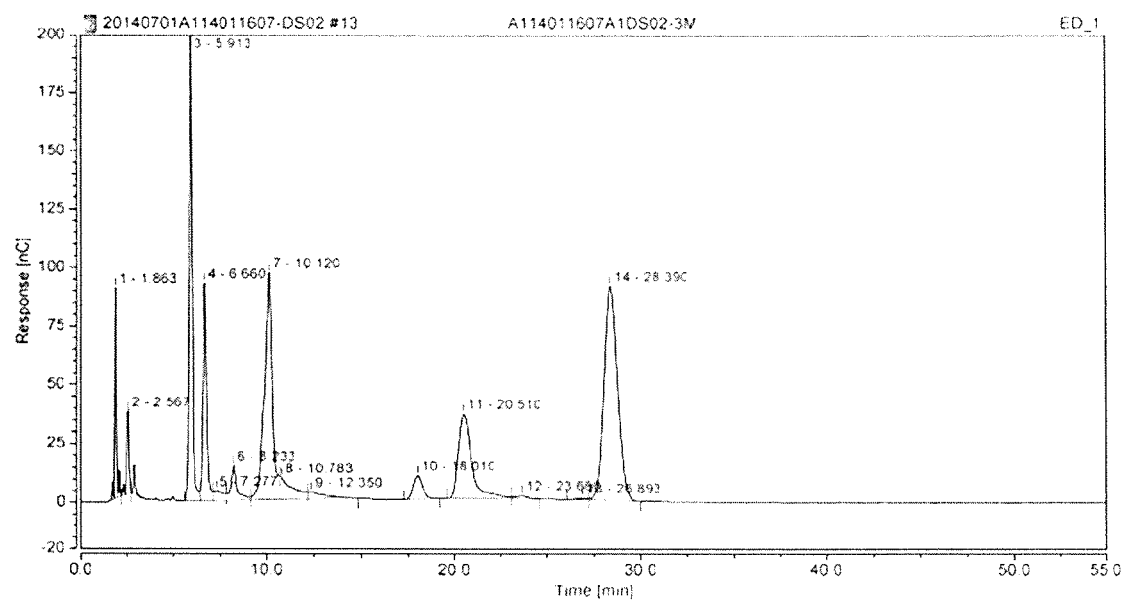
FIGS. 1 to 3 show the ion chromatography spectrograms of the soybean seed extract (GMA1) according to the invention.
Figure 2:
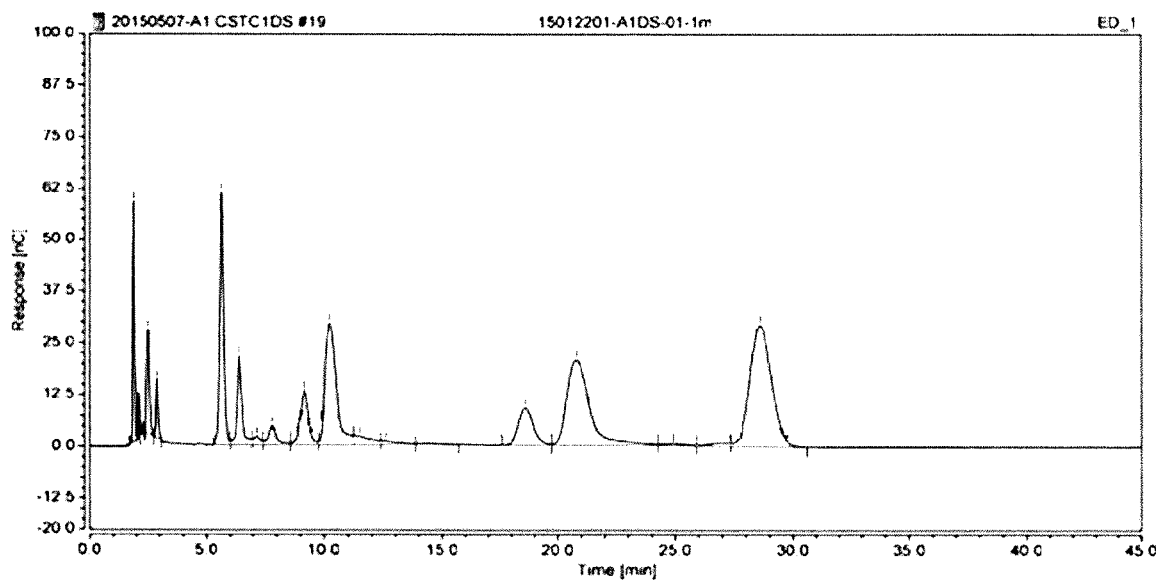
Figure 3:
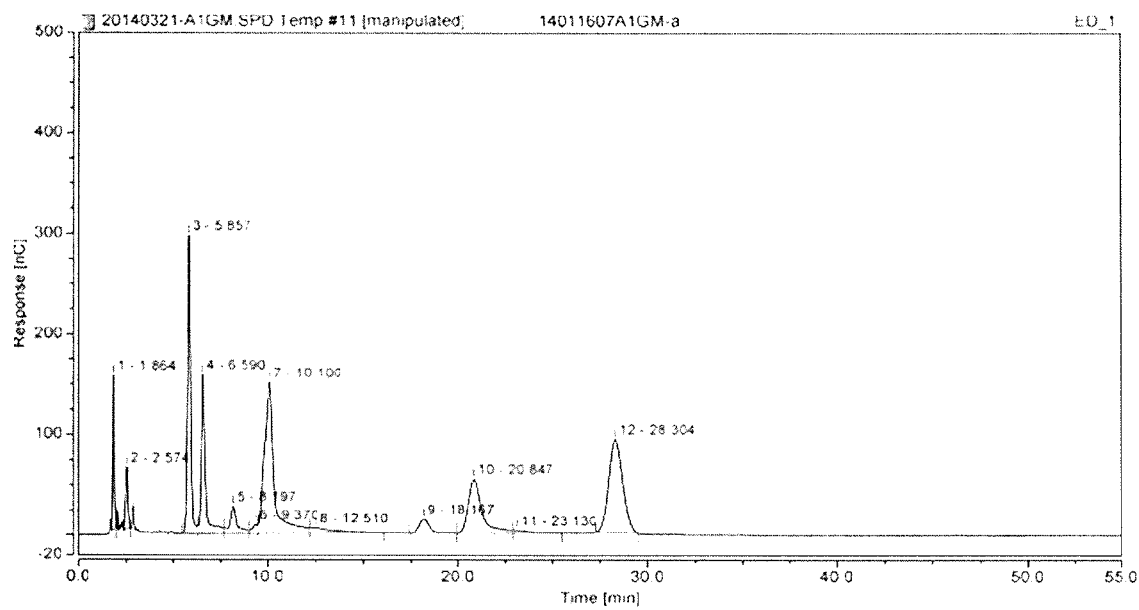

The spectrograms obtained are shown in FIGS. 1 to 3. The peak time is shown in Table 1.

TABLE 1

| | Peak time (minutes) | | | | | |
|---|---|---|---|---|---|---|
| | Peak 1 | Peak 2 | Peak 3 | Peak 4 | Peak 5 | Internal standard |
| FIG. 1 | 5.913 | 6.660 | 10.120 | 18.010 | 20.510 | 28.390 |
| FIG. 2 | 5.660 | 6.420 | 10.244 | 18.600 | 20.784 | 28.597 |
| FIG. 3 | 5.857 | 6.590 | 10.100 | 18.167 | 20.847 | 28.304 |

Preferably, the extract composition according to the invention further comprises a soybean seed vapor fraction, which soybean seed vapor fraction is prepared by a process comprising steps of:

(i) providing soybean seeds in a second extracting solution, which second extracting solution is water or an alcohol solution containing alcohol at the concentration lower than about 15 wt %; and (ii) extracting the soybean seeds with the second extracting solution at a barometric pressure lower than about 1 atm and at a temperature lower than about 110° C. and collecting the vapor fraction.

The second extracting solution for preparing the soybean seed vapor fraction according to the invention is water or an alcohol solution containing alcohol at the concentration lower than about 15 wt %; preferably water. The kind of the alcohol can be the same to that of the extracting solution for preparing the soybean seed extract and is not repeated herein.

The alcohol of the second extracting solution is the alcohol solution with a concentration lower than about 15% (v/v); preferably lower than about 10% (v/v); more preferably lower than about 5% (v/v).

The process for preparing the soybean seed vapor fraction according to the invention comprises the step (ii) extracting the soybean seeds with the second extracting solution at a barometric pressure lower than about 1 atm and at a temperature lower than about 110° C. and collecting the vapor fraction. The manner of extracting can be the same to that of preparing the soybean seed extract, provided that the soybean seed vapor fraction is vaporized at a barometric pressure lower than about 1 atm and at a temperature lower than about 110° C. The vapor fraction can be collected in a liquid form by chilling the vapor.

In a preferred embodiment of the invention, a process of vaporizing the soybean seeds at a given barometric pressure and temperature, and collecting said vapor fraction by chilling the vapor can be performed in a rotary evaporator where the vapor is evaporated to the condensing tube supplied with cold water, and then the vapor is chilled by passing through the condensing tube to collect the vapor fraction in a liquid form. The manipulation is simple and the cost is low.

According to the invention, the ratio (w/v) of the soybean seeds and the second extracting solution is not specifically restricted. In one preferred embodiment of the invention, the ratio (w/v) of the soybean seeds and the second extracting solution is about 1:1 to about 1:30; more preferably about 1:5 to about 1:20; and most preferably about 1:10.

The temperature of extraction in the step (ii) according to the invention is lower than about 110° C.; preferably from about 60° C. to about 110° C.

In one preferred embodiment of the invention, the extraction step (ii) can be repeated, and the soybean seed vapor fraction is collected by merging.

In one preferred embodiment of the invention, the soybean seed vapor fraction is subjected to an ion chromatography assay with CarboPac PA1 Analytical (4×250 mm) column. The mobile phase is 87% water and 13% 500 mM NaOH; the internal standard is maltose monohydrate. The isocratic elution is applied with the low rate of 1.0 ml/min and the cycle of 0.5 second. In every cycle, the assay is conducted with the relative potential of 0.1 V at 0.00 second to 0.2 second; 0.1 V at 0.2 second to 0.4 second; −2.0 V at 0.41 second to 0.42 second; 0.6 V at 0.43 second; −0.1 V at 0.44 second to 0.5 second, and the total assay duration is 55 minutes.

Figure 4:
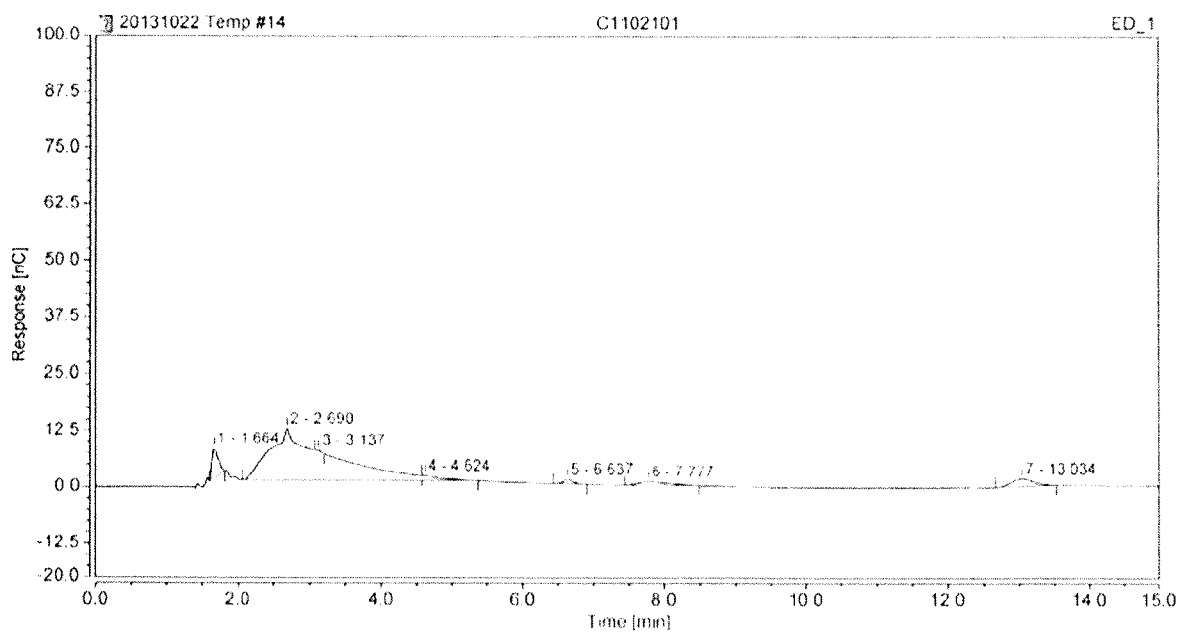
FIGS. 4 to 6 show the ion chromatography spectrograms of the soybean seed vapor fraction (GMC1) according to the invention.
Figure 5:
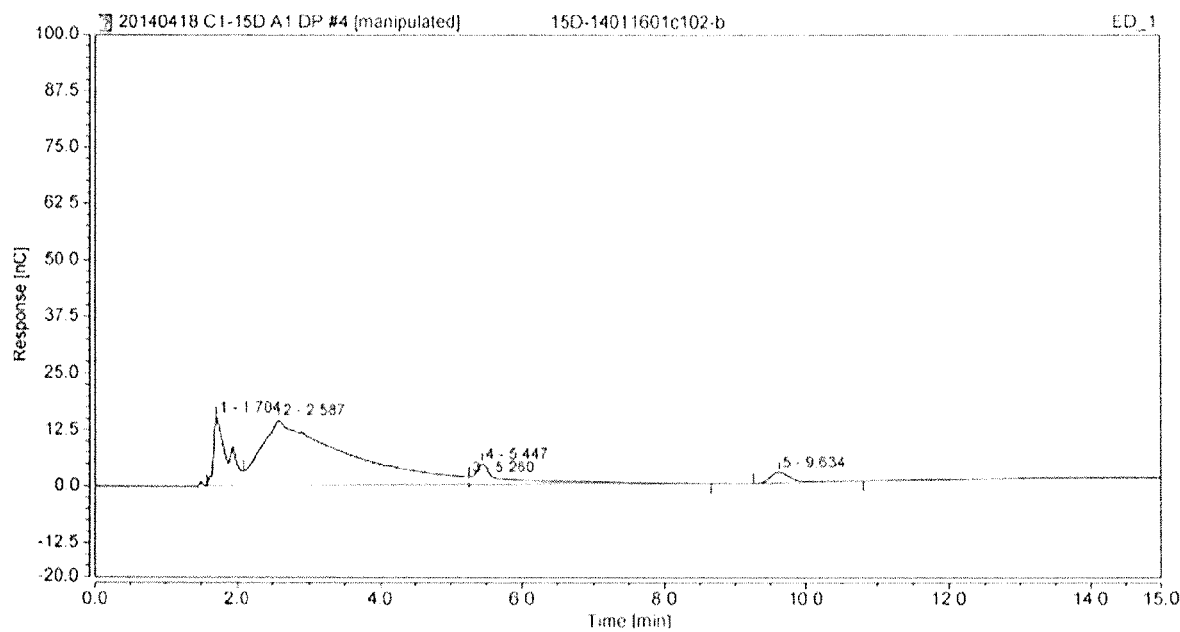
Figure 6:
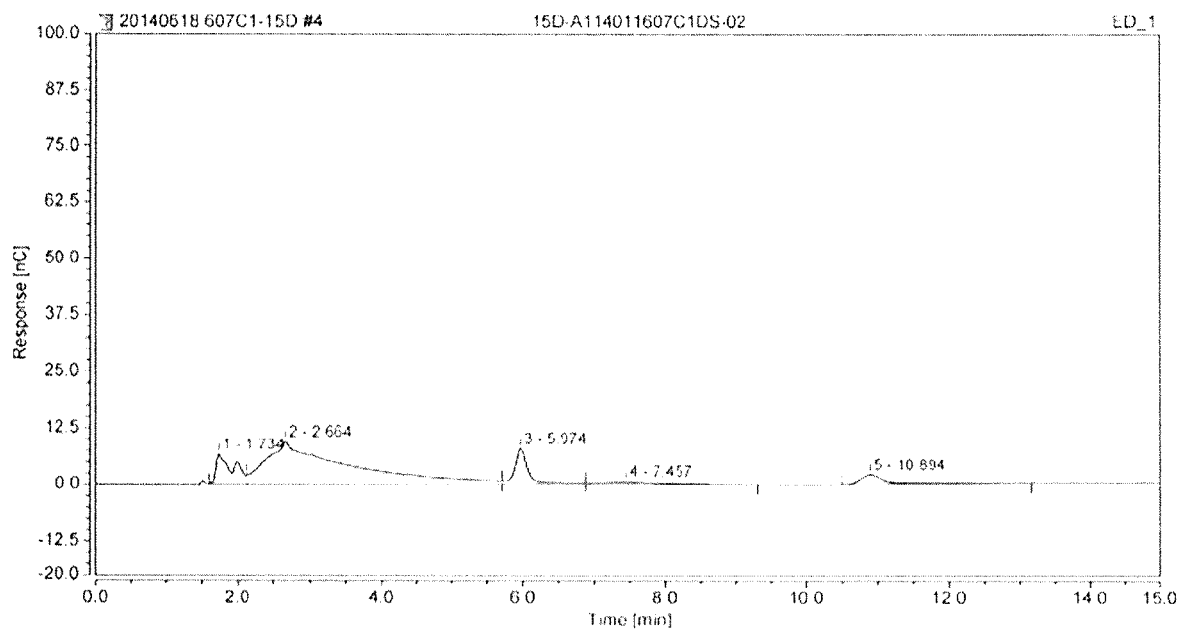

The spectrograms obtained are shown in FIGS. 4 to 6. The peak time is shown in Table 2.

TABLE 2

| | Peak time |
|---|---|
| FIG. 4 | 2.690 |
| FIG. 5 | 2.587 |
| FIG. 6 | 2.664 |

In one embodiment of the invention, the content of the soybean seed extraction based on the extract composition is from about 0.001% wt to about 10% wt; preferably from about 0.01% wt to about 5% wt; more preferably from about 0.001% wt to about 1.5% wt. In another aspect, the content of the soybean seed vapor fraction based on the extract composition is from about 0.04% wt to about 99.999% wt; preferably from about 10% wt to about 99.9% wt; more preferably from about 30% wt to about 99% wt.

The extraction composition according to the invention is preferably a pharmaceutical composition, food composition or a cosmetic composition.

The pharmaceutical composition according to the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art.

The external route as used herein is also known as local administration, includes but is not limited to administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets or liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution. The aerosol composition may optionally contain additional formulation excipients well known in the art such as surfactants e.g. oleic acid or lecithin and cosolvents e.g. ethanol.

Topical preparations may be administered by one or more applications per day to the affected area; over the skin areas occlusive dressings may advantageously be used. Continuous or prolonged delivery may be achieved by an adhesive reservoir system.

The cosmetic composition according to the invention may be an aqueous phase formulation consisting essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms, such as propylene glycol, ethylene glycol, 1,3-butylene glycol or dipropylene glycol, C3-C4 ketones and C2-C4 aldehydes, and glycerin. Such an aqueous formulation preferably is in a form of aqueous gel or hydrogel formulation. The hydrogel formulation comprises a thickening agent to thicken the liquid solution. Examples of the thickening agents include, but are not limited to, carbomers, cellulose base materials, gums, algin, agar, pectins, carrageenan, gelatin, mineral or modified mineral thickeners, polyethylene glycol and polyalcohols, polyacrylamide and other polymeric thickeners. The thickening agents which give the stability and optimal flow characteristics of the composition are preferably used.

The cosmetic composition according to the present invention may be in a form of emulsion or cream formulation. It can contain emulsifying surfactants. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of said reference, for the anionic and nonionic surfactants.

The surfactants preferably used in the cosmetic composition according to the invention are chosen from: nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated fatty esters of C1-C6 alkyl glucose, and mixtures thereof; anionic surfactants: C16-C30 fatty acids neutralized with amines, aqueous ammonia or alkaline salts, and mixtures thereof. Surfactants which make it possible to obtain an oil-in-water or wax-in-water emulsion are preferably used.

The cosmetic composition according to the invention may further comprise an effective amount of a physiologically acceptable antioxidant selected from the group consisting of butylated p-cresol, butylated hydroquinone monomethyl ether, and a tocopherol.

The cosmetic composition according to the invention may further comprise natural or modified amino acid, natural or modified sterol compound, natural or modified collagen, silk protein or soy protein.

The cosmetic composition according to the invention is preferably formulated for topical application to keratin materials such as the skin, the hair, the eyelashes or the nails. They may be in any presentation form normally used for this type of application, especially in the form of an aqueous or oily solution, an oil-in-water or water-in-oil emulsion, a silicone emulsion, a microemulsion or nanoemulsion, an aqueous or oily gel or a liquid, pasty or solid anhydrous product.

The cosmetic composition according to the invention may be more or less fluid and may have the appearance of a white or colored cream, an ointment, a milk, a lotion, a serum, a paste, a mousse or a gel. It may optionally be topically applied onto the skin in the form of an aerosol, a patch or a powder. It may also be in solid form, for example, in the form of a stick. It may be used as care products and/or as makeup products for the skin. Alternatively, it may be formulated as shampoos or conditioners.

In known fashion, the cosmetic composition according to the invention may also contain additives and adjuvants that are common in cosmetics, such as hydrophilic or lipophilic gelling agents, preservatives, antioxidants, solvents, fragrances, fillers, pigments, odor absorbers and dyestuffs.

The extract composition can be added to a conventional food composition (i.e. the edible food or drink or precursors thereof) in the manufacturing process of the food composition. Almost all food compositions can be supplemented with the extract composition of the invention. The food compositions that can be supplemented with the extract composition of the invention include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The present invention is also to provide use of the extract composition as mentioned above in the manufacture of a medicament of promoting wound healing.

The invention also provides a method for promoting wound healing in a subject in need of such promotion comprising administering to said subject an effective amount of the extract composition as mentioned above and optionally a pharmaceutically acceptable carrier or excipient.

Preferably, the extract composition according to the invention is promoting wound healing by promoting skin cell migration. In one preferred embodiment of the invention, the extract composition is able to promoting keratinocyte migration, and the skin cell is preferably a keratinocyte. In another aspect, in an animal model according to the incention, the extract composition is able to promoting wound healing in a diabetic patient, and the wound is preferably a diabetic wound.

In one embodiment of the invention, the composition comprising the soybean seed extract and soybean seed vapor fraction has significant effect ($p<0.5$) in would closure, compared to cream base, and the soybean seed extract slightly exhibits better outcome in wound closure than the soybean seed vapor fraction.

In one another embodiment of the invention, different dose levels of the soybean seed extract are used in combined with the soybean seed vapor fraction for investigating the effect on diabetic wound healing. The results show that for wound healing, the combination effects of the soybean seed extract and the soybean seed vapor fraction are better than the soybean seed vapor fraction alone. The most effective combination treatment is found in the highest dosage of the soybean seed extract.

In one embodiment of the invention, the soybean seed extract and soybean seed vapor fraction are used alone or in combination for assaying the effects on promoting skin keratinocyte migration. The results show that for promoting skin keratinocyte migration, the combination effects of the soybean seed extract and the soybean seed vapor fraction are better than the soybean seed extract or the soybean seed vapor fraction alone.

The present invention is also to provide use of the extract composition as mentioned above in the manufacture of a medicament of promoting neuron cell proliferation and/or treating brain diseases and/or neurodegenerative diseases.

The invention also provides a method for promoting neuron cell proliferation and/or treating brain diseases and/or neurodegenerative diseases in a subject in need of such promotion and/or treatment comprising administering to said subject an effective amount of the extract composition as mentioned above and optionally a pharmaceutically acceptable carrier or excipient.

Preferably, the neuron cell is a central nervous system cell; more preferably is a brain neuron cell; still more preferably is a neuroblastoma cell.

The brain diseases and/or neurodegenerative diseases according to the invention are preferably selected from the group consisting of vascular dementia, Alzheimer's disease, Parkinson's disease, cerebral vascular disease, inflammatory brain injury, brain damage surrounding inflammatory response, brain lesions, cerebral hematoma, swelling ventricle and ventricular dilatation.

In one embodiment of the invention, the soybean seed extract, soybean seed vapor fraction and extraction composition comprising the soybean seed extract and soybean seed vapor fraction are used to treat human neuroblastoma cell. The results show that the cell viability rate is significantly increased after treated with the soybean seed extract, soybean seed vapor fraction and extraction composition comprising the soybean seed extract, soybean seed vapor fraction. Therefore, the soybean seed extract and soybean seed vapor fraction and extraction composition comprising the soybean seed extract and soybean seed vapor fraction have effects on promoting neuron cell proliferation.

In one another embodiment of the invention, in a radial arm maze test of a dementia rat animal model, after the treatment of the extract composition comprising the soybean seed extract and soybean seed vapor fraction, total memory errors and reference memory errors are significantly lower than those of an untreated group. It shows that the extract composition comprising the soybean seed extract and soybean seed vapor fraction has the effect on treating dementia rats.

In one another embodiment of the invention, in a radial arm maze test of a dementia rat animal model, after the treatment of the extract composition comprising the soybean seed extract and soybean seed vapor fraction, total memory errors and reference memory errors are significantly lower than those of an untreated group. It shows that the extract composition comprising the soybean seed extract and soybean seed vapor fraction has the effect on treating dementia rats.

In a vascular dementia model, the results show that the memory impairment caused by vascular dementia is significantly improved after the extract composition treatments according to the invention. The soybean seed vapor fraction and the extract composition comprising the soybean seed extract and soybean seed vapor fraction both improve the working memory errors, reference memory errors and total memory errors. Compared to the soybean seed vapor fraction alone, the extract composition comprising the soybean seed extract and soybean seed vapor fraction has better effect on treating memory impairment caused by vascular dementia.

The present invention is also to provide use of the extract composition as mentioned above in the manufacture of a medicament of treating breast cancer.

The invention also provides a method for treating breast cancer in a subject in need of such treatment comprising administering to said subject an effective amount of the extract composition as mentioned above and optionally a pharmaceutically acceptable carrier or excipient.

Preferably, the breast cancer is the breast cancer with p53 mutant type.

In one preferred embodiment of the invention, a p53 mutant type of human breast cancer cell line is used to establish an animal model to simulate the situation in the primary site for observing the tumor growth in mice. In the case of simulating the administration in human, different concentrations of the extract composition according to the present invention is administrated. It shows that the extract composition according to the invention has effect on inhibiting tumor growth rate in the tumor-bearing mice.

The present invention is also to provide use of the extract composition as mentioned above in the manufacture of a medicament of reducing side effects of interfering with DNA and/or RNA replication drugs, and/or enhancing pharmaceutical effects of interfering with DNA and/or RNA replication drugs.

The invention also provides a method for reducing side effects of interfering with DNA and/or RNA replication drugs and/or enhancing pharmaceutical effects of interfering with DNA and/or RNA replication drugs in a subject in need of such reduction and/or enhancement comprising administering to said subject an effective amount of the extract composition as mentioned above and optionally a pharmaceutically acceptable carrier or excipient.

The term "interfering with DNA and/or RNA replication drugs" as used herein refers to drugs which kill a tumor cell by preventing the process of DNA and/or RNA replication essential in mitosis. Preferably, the interfering with DNA and/or RNA replication drugs are cyclophosphamide, temozolomide, hexamethylmelamine, platinum complexes, bleomycin, vinblastine, vincristine, paclitaxel, docetaxel, folic acid antagonists, purine antagonists, or pyrimidine antagonists.

In one preferred embodiment of the invention, a human breast cancer cell line is used to establish an animal model to simulate the situation in the primary site. Compared to the tumor-bearing mice administrated with cyclophosphamide, the extract composition according to the invention has enhancing effect of the chemotherapy drug on inhibiting tumor growth rate in the tumor-bearing mice. The extract composition according to the invention inhibits tumor growth, has enhancing effect of the chemotherapy drug on eliminating tumor size, and relieves pain by reducing tumor compression, thus the patient can have better life quality.

The following examples are provided to aid those skilled in the art in practicing the present invention.

EXAMPLES

Soybean Seed Extract (GMA1)

Seeds of soybean (*Glycine max* (L.) Merr.) were grinded into power, and 70% by weight of ethanol or distilled water was applied as an extracting solution; the ratio (w/v) of the soybean seeds and the extracting solution was about 1:10. The soybean seeds were extracted at a barometric pressure about 1 atm and at a temperature of about 45° C. to obtain an crude extract. The solids were removed from the crude extract to obtain a liquid portion. The liquid portion was further concentrated by a reduced-pressure condenser to obtain a concentrated solid portion. The concentrated solid portion was further dried at 70° C.

Soybean Seed Vapor Fraction (GMC1)

Seeds of soybean (*Glycine max* (L.) Merr.) were grinded into power, and 2% by weight of ethanol or distilled water was applied as a second extracting solution; the ratio (w/v) of the soybean seeds and the second extracting solution was about 1:10. The vapor fraction was obtained by vaporizing the soybean seeds in a rotary evaporator (EYELA N-1000S, 1000S-W) at a pressure of lower than 1 atm and a temperature of 90° C., and passing through a condensing tube supplied with cold water.

Analysis of the Soybean Seed Extract (GMA1) and Soybean Seed Vapor Fraction (GMC1)

The obtained soybean seed extract (GMA1) and soybean seed vapor fraction (GMC1) were subjected to an ion chromatography assay with CarboPac PA1 Analytical (4×250 mm) column. The mobile phase was 87% water and 13% 500 mM NaOH; the internal standard is maltose monohydrate. The isocratic elution was applied with the low rate of 1.0 ml/min and the cycle of 0.5 second. In every cycle, the assay was conducted with the relative potential of 0.1 V at 0.00 second to 0.2 second; 0.1 V at 0.2 second to 0.4 second; −2.0 V at 0.41 second to 0.42 second; 0.6 V at 0.43 second; −0.1 V at 0.44 second to 0.5 second, and the total assay duration was 55 minutes.

The spectrograms of the soybean seed extract (GMA1) are shown in FIGS. 1 to 3. The peak time is shown in Table 1.

The spectrograms of the soybean seed vapor fraction (GMC1) are shown in FIGS. 4 to 6. The peak time is shown in Table 2.

The Soybean Seed Extract (GAA 1) Contains Very Small Amount of Isoflavones and the Soybean Seed Vapor Fraction (GMC1) Contains No Isoflavones A high performance liquid chromatography (HPLC) was applied to assay if the soybean seed extract (GMA1) and soybean seed vapor fraction (GMC1) contained isoflavones.

The condition of HPLC was listed as follows:
Apparatus: Hitachi HPLC CM5000 Series; pump: CM5110; detector: CM5430 (DAD); automatic feeding system: CM5210; column oven: CM5310; software: OpenLab. Column: RP $C_{18}$, 4.6×250 mm 5 μm; detection wavelength: UV 254 nm; flow rate: 0.8 min/ml; column oven temperature: 30° C.; gradient: as shown in Table 3.

TABLE 3

| Time (minute) | Solvent (%) | |
| --- | --- | --- |
|  | Elution 1 | Elution 2 |
| 0 | 95 | 5 |
| 10 | 85 | 15 |
| 25 | 77 | 23 |
| 35 | 72 | 28 |
| 40 | 20 | 80 |
| 45 | 20 | 80 |
| 46 | 95 | 5 |
| 55 | 95 | 5 |

Figure 7:
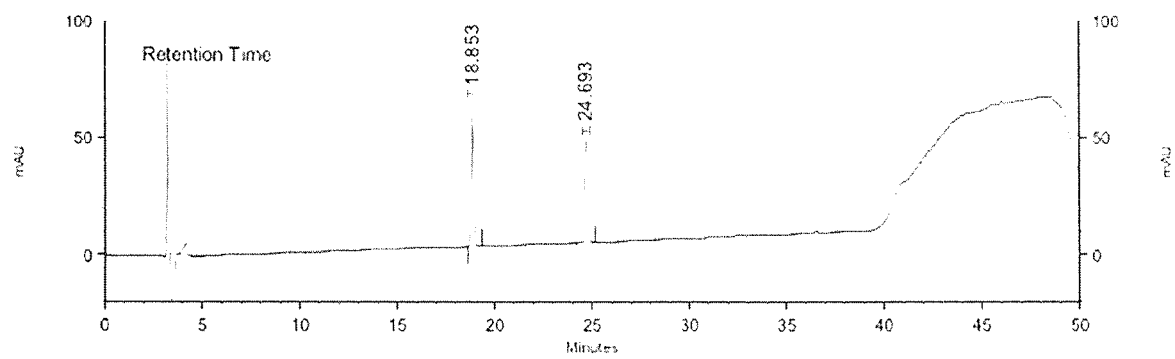
FIG. 7 shows the high performance liquid chromatography (HPLC) spectrogram of the isoflavones standard.

Elution 1: 1% formic acid + 0.01% trifluoroacetic acid (TFA) in water
Elution 2: 1% formic acid + 0.01% trifluoroacetic acid in acetonitrile The HPLC spectrogram of the isoflavones standard is shown in FIG. 7, and peaks occurred at retention time of 18.853 minutes and 24.693 minutes.

Figure 8:
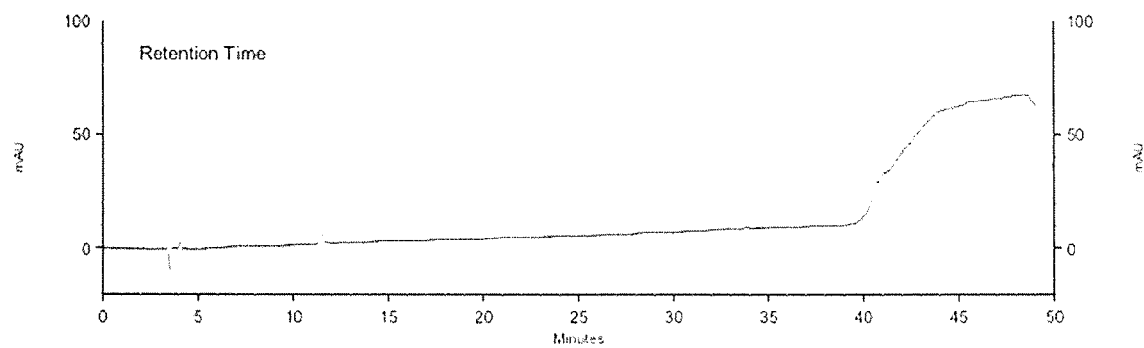
FIG. 8 shows the HPLC spectrogram of the soybean seed vapor fraction (GMC1).

The HPLC spectrogram of the soybean seed vapor fraction (GMC1) is shown in FIG. 8, and no peaks occurred.

Figure 9:
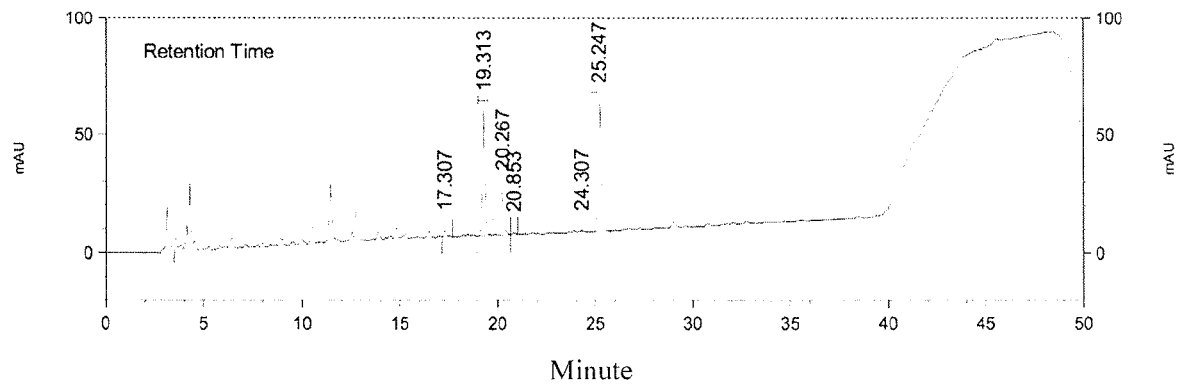
FIG. 9 shows the HPLC spectrogram of the extract composition containing 0.3 part by weight of the soybean seed extract (GMA1) and 1 part by weight of the soybean seed vapor fraction (GMC1).

The HPLC spectrogram of an ointment containing 0.3 part by weight of the soybean seed extract (GMA1) and 1 part by weight of the soybean seed vapor fraction (GMC1) is shown in FIG. 9, and peaks occurred at retention time of 17.307 minutes, 19.313 minutes, 20.267 minutes, 20.853 minutes, 24.307 minutes and 25.247 minutes.

By comparing FIGS. 7 to 9, it shows that no peaks occur in the HPLC spectrogram of the soybean seed vapor fraction (GMC1) in FIG. 8, and thus the soybean seed vapor fraction (GMC1) contains no isoflavones; the peaks corresponding to the isoflavones fingerprint absorption peaks occur at a very small amount in the HPLC spectrogram of the extract composition containing 0.3 part by weight of the soybean seed extract (GMA1) and 1 part by weight of the soybean seed vapor fraction (GMC1) in FIG. 9. After conversion, the content of daidzin is 4.8 μg/ml and the content of genistin is 8.23 μg/ml, which contents are far away from the pharmaceutically effective amount of isoflavones. Therefore, the soybean seed extract (GMA1) only contains a very small amount of isoflavones, and the pharmaceutical effect thereof is not exhibited by the very small amount of isoflavones.

Extract Composition for Promoting Wound Healing
Material and Method:

Approximately 8 weeks old, with body weight rages of 250 g to 300 g SD male rats were obtained from National Laboratory Animal Center, Taiwan. After 7 days of quarantine, the rats were moved until the body weight over 350 g. The rats were identified by ear notch of the animals. Each cage tag was labeled with the cage number, study number, sex and group name. The rats were housed 2 per cage in polycarbonate cage in the AAALAC accredited animal facility.

The environment conditions were: temperature: 21±2° C.; humidity: 50±20%; light cycle: in light for 12 hours and in dark for 12 hours. Laboratory Rodent Diet 5001 (PMI$^R$ Nutrition International, Inc., MO, USA) were supplied ad libitum throughout the study period. Tap water was supplied ad libitum via bottles attached to the cages.

Experimental Methods:
Samples (test articles) were prepared according to Table 4.

TABLE 4

| group | animal/number/sex | Test article and dose |
| --- | --- | --- |
| Experimental 1 | | |
| 1 | Diabetic rats/5/male | Cream base |
| 2 | Diabetic rats/5/male | CGS-21680 10 μg/wound |
| 3 | Diabetic rats/5/male | GMC1 |
| 4 | Diabetic rats/5/male | 0.3% GMA1 |
| Experimental 2 | | |
| 1 | Diabetic rats/5/male | Cream base |
| 2 | Diabetic rats/5/male | CGS-21680 6.7 μg/wound |
| 3 | Diabetic rats/5/male | GMC1 |
| 4 | Diabetic rats/5/male | GMC1 + 0.009% GMA1 |
| 5 | Diabetic rats/5/male | GMC1 + 0.045% GMA1 |
| 6 | Diabetic rats/5/male | GMC1 + 0.09% GMA1 |

CGS-21680: Specific adenosine $A_{2A}$ subtype receptor agonist, prepared by adding 1.67 mg of CGS-21680 in 248.4 g of cream base.

Diabetic rats: The rats with body weight over 300 g were administrated with one dose of Streptozotocin (STZ, 65 mg/kg) by intravenous injection. The STZ-induced rats with high blood sugar (over 300 mg/dL) for 2 months were selected to conduct the wound closure test.

Trauma surgeries for diabetic rats: The diabetic rats with weight lower than 300 g were eliminated and the rest were randomized into 6 groups. The rats were then anesthetized with pentobarbital and hairs on surgical area (dorsal area) were removed. Three skins on the dorsal medium areas (4, 6 and 8 cm from the midpoint of two scapulas) in each rat were excised (full thickness) using round cutting blades.

Medication and wound closure measurement: The animals were weighed and the area of wounds was measured every other day for evaluation of wound closure. Medications were applied to each wound twice a day and the wounds were covered with cheesecloth. The hoods were worn on the necks of the rats to prevent the wounds from receiving animal scratches. For wound closure measurement, the wound pictures were taken at day 4, 6, 8, 10, 12 and 14. When taking pictures, a standard ruler was placed beside the wounds. Before analyzing the wounds with Image pro (Media cybernetics), length was standardized with the standard ruler in the picture to avoid the errors caused by different picturing distances.

Data analysis and statistics: Three wound areas on the rats' backs were analyzed by Image pro. The original wound areas were the areas of day zero. The original wound areas minus the wound areas at different time points and then divided by the original wound areas to get the wound closure percentages. The mean of three wound closure percentages of each rat represents the wound closure of each rat. The data was shown as mean±standard error (SEM). The p-values of the testing results were calculated by t-test in statistics software (SYSTAT, Systat software Inc). $P<0.05$ means there is a significant difference, and it is marked with *. $P<0.01$ means there is a very significant difference, and it is marked with . $P<0.001$ means there is an extremely significant difference, and it is marked with *.

Figure 10:
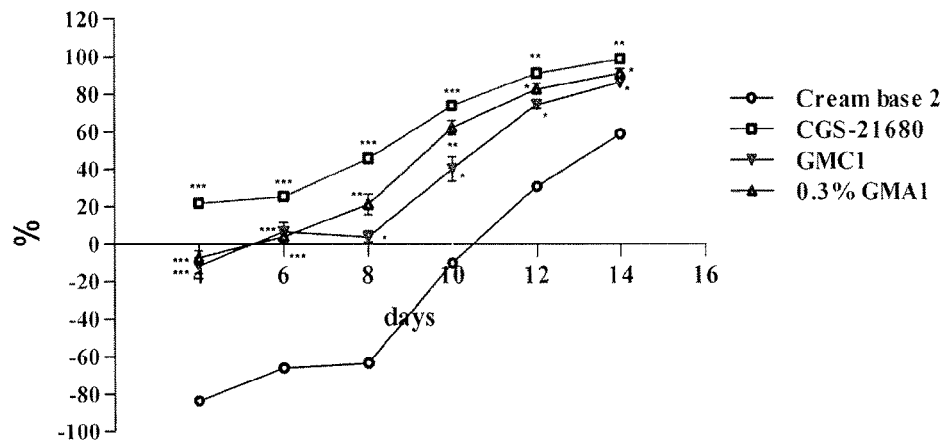
FIG. 10 shows the effects of GMA1 and GMC1 on diabetic wound healing. To investigate whether GMC1 and GMA1 have effects on improving wound closure, a STZ-induced diabetic rat model was utilized. For comparison, two groups treated with cream base and CGS-21680 were also conducted. The results show that both 0.3% GMA1 and GMC1 are effective on would closure, compared to cream base alone, and 0.3% GMA1 treated group slightly exhibits better outcome in wound closure than GMC1.

Result:
After medication, wound areas were measured at different time points and wound closure percentages were analyzed with statistic software and shown in Table 5 and FIG. 10. On day 4, the wound closure percentages for groups cream base, CGS-21680, GMC1, and 0.3% GMA1 are −83.33±6.60(%), 21.87±5.61(%), −11.44±4.34(%) and −7.09±3.65(%), respectively. All treatment groups are significantly different from the cream base group during the whole experimental period. On day 8 to day 10, the wound closure percentages are mostly enhanced with GMC1 and 3% GMA1 treated groups, changed from −4.10±3.04(%) to 40.15±6.47 (%) and 21.21±5.52(%) to 62.19±3.85(%), respectively. On day 14, the wound closure percentages of GMC1 and 3% GMA1 are significantly enhanced, 86.20±1.88(%) and 91.21±2.23 (%), respectively, and compared to cream base, 58.92±13.14 (%).

Extract Composition for Promoting Skin Cell Migration

HaCaT cells (human skin keratinocytes) were used for assaying the effect of the extract composition on promoting skin cell migration.

Samples of the cell migration assay were:

A1-0.3: containing 0.3 μg/mL of GMA1

A1-0.3-CSTC-2500X: containing 2500-fold diluted GMC1 and 0.3 μg/mL of GMA1

Cell line: HaCaT

Medium: DMEM containing 10% fetal bovine serum

Positive control: CGS-21680

TABLE 5

Comparison of wound closure percentages of diabetic rats treated with GMC1 and 0.3% GMA1

| Day | Cream base Mean ± SEM | CGS-21680 Mean ± SEM | GMC1 Mean ± SEM | 0.3% GMA1 Mean ± SEM |
|---|---|---|---|---|
| 4  | −83.33 ± 6.60  | 21.87 ± 5.61 *** | −11.44 ± 4.34 *** | −7.09 ± 3.65 *** |
| 6  | −65.84 ± 11.19 | 25.45 ± 4.46 *** | 6.74 ± 4.86 ***   | 4.15 ± 3.19 *** |
| 8  | −63.32 ± 23.22 | 45.88 ± 4.28 *** | 4.10 ± 3.04 *     | 21.21 ± 5.52 ** |
| 10 | −10.08 ± 16.87 | 93.80 ± 2.79 *** | 40.15 ± 6.47 *    | 62.19 + 3.85 ** |
| 12 | 30.85 ± 20.08  | 91.15 ± 2.72 **  | 74.36 ± 2.04 *    | 82.71 ± 2.82 * |
| 14 | 58.92 ± 13.14  | 98.74 ± 0.60 **  | 86.20 ± 1.88 *    | 91.21 ± 2.23 |

Remark: Each value represents the mean ± SEM. The comparison values between two groups are significantly different at
** p < 0.01 and
*** p < 0.001 by Student's t test.

The results showed that both 0.3% GMA1 and GMC1 are effective in would closure, compared to cream base alone, and 0.3% GMA1 treated group slightly exhibits better outcome in wound closure than GMC1.

The optimal combination of GMA1 and GMC1 in promoting diabetic wound closure was investigated. Different dose levels of GMA1, 0.009%, 0.045% and 0.09% were used in combined with GMC1. For comparison, cream base and CGS-21680 groups were also incorporated.

Figure 11:
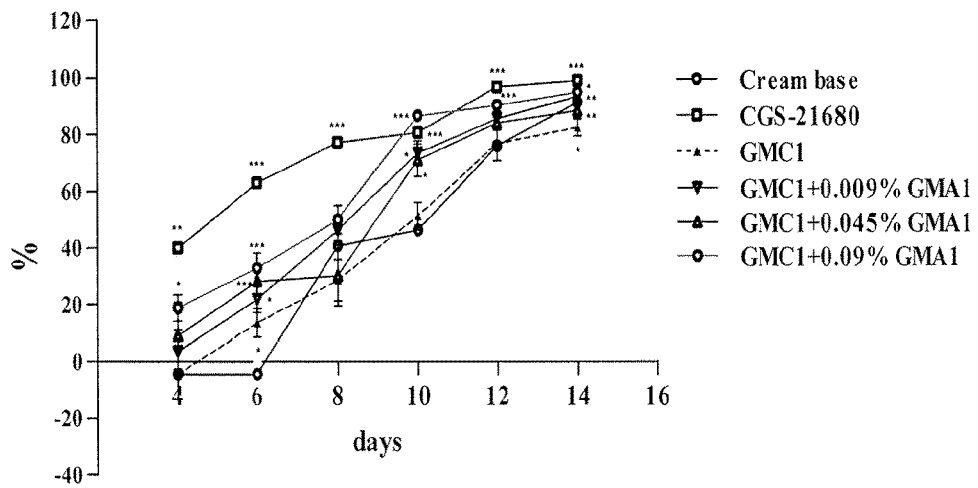
FIG. 11 shows the effects of different dosages of GMA1 in combination with GMC1 on diabetic wound healing. Experiments were conducted to study the best combination of GMA1 and GMC1 in diabetic wound closure.

After medication, wound areas were measured at different time points and wound closure percentages were analyzed with statistic software and shown in Table 6 and FIG. 11. As shown in Table 6 and FIG. 11, by comparing to cream base groups, an increase in statistical significance is observed with increasing GMA1 dose levels in combination drug groups, 0.009%, 0.045% and 0.09% of GMA1. The results show that for wound healing, the combination effects of the dose levels, 0.009%, 0.045% and 0.09%, of GMA1 with GMC1 are better than GMC1 alone. The most effective combination treatment is found in the highest dosage of GMA1 (0.09%).

Cell culture: HaCaT cells were cultured in DMEM containing 10% fetal bovine serum at 37° C. and 5% $CO_2$, and subcultured twice weekly.

Wound healing assay: Oris Cell Migration Assay kit was applied. The cells were planted into a 96-well plate ($4\times10^4$ cells/well) with a stopper and cultured in a carbon dioxide incubator. After cultured overnight, the stopper was pulled out to produce wounds and new medium or medium containing test articles or CGS-21680 (positive control) were added. After treatment for 0, 16 and 24 hours, the cells were observed under an optical microscope at 100 times magnification observation and photographs were taken for monitoring wound healing.

Analysis: Software of image j was applied to quantify the wound healing area. Area at 0 hour was taken as the original size of the wound. After a period of time, the wound area was gradually reduced, and the extent of wound healing was quantified by calculating the wound area relative to the original area at 0 hour (healing rate=difference between the area at T16 or T24 time point and that at T0/T0 area), to assess the effect of the drugs on HaCaT cell migration activity.

TABLE 6

Comparison of wound closure percentages of diabetic rats treated with 0.009%~0.09% of GMA1 in combined with GMC1

| Days | Cream base Mean ± SEM | CGS-21680 Mean ± SEM | GMC1 Mean ± SEM | GMC1 + 0.009% GMA1 Mean ± SEM | GMC1 + 0.045% GMA1 Mean ± SEM | GMC1 + 0.09% GMA1 Mean ± SEM |
|---|---|---|---|---|---|---|
| 4  | −4.45 ± 7.92 | 40.02 ± 5.03** | −4.47 ± 8.88 | 3.66 ± 7.39 | 9.15 ± 11.71 | 18.90 ± 4.66* |
| 6  | −4.3 ± 4.42  | 63.09 ± 2.58*** | 13.59 ± 5.05* | 21.97 ± 4.69* | 28.33 ± 4.50*** | 32.99 ± 5.40*** |
| 8  | 40.85 ± 6.00 | 77.21 ± 2.44*** | 28.61 ± 7.35 | 46.52 ± 4.08 | 30.25 ± 10.69 | 50.11 ± 5.00 |
| 10 | 46.51 ± 4.55 | 80.93 ± 2.08*** | 51.35 ± 4.86 | 73.57 ± 4.18* | 71.09 ± 5.62* | 86.68 ± 0.93*** |
| 12 | 76.05 ± 2.30 | 96.91 ± 1.08*** | 76.84 ± 5.98 | 85.78 ± 2.38** | 84.23 ± 2.55** | 90.49 ± 1.27*** |
| 14 | 91.39 ± 1.23 | 99.17 ± 0.54*** | 82.58 ± 3.01* | 93.61 ± 2.39 | 88.57 ± 2.44 | 95.02 ± 0.65* |

Remark:
Each value represents the means ± SEM.
The comparison values between two groups are significantly different at p < 0.01 and *p < 0.001 by student's t test.

Statistics: Each group was repeated at least four times. The data was shown as mean±standard error (SEM). The significance of the testing results was calculated by t-test.

Figure 12:
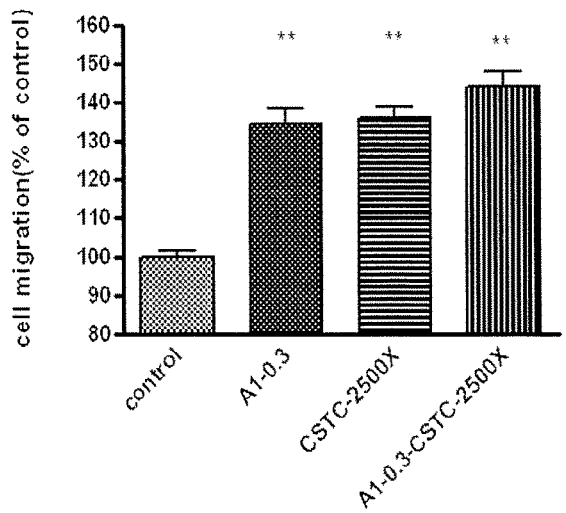
FIG. 12 shows the effects of combinations of the soybean seed extract and soybean seed vapor fraction on HaCaT cell migration.

Result:

HaCaT cell migration assay is used for comparing the effects of GMC1 and GMA1 on promoting wound healing. The combination effects of 2500-fold diluted GMC1 and 0.3 µg/mL of GMA1 (A1-0.3-CSTC-2500X) are better than A1-0.3 alone on promoting HaCaT cell migration (FIG. 12).

Extract Composition for Promoting Neuron Cell Proliferation

Material and Method:

Cell line: Human neuroblastoma cell IMR-32 (purchased from Food Industry Research and Development Institute, Taiwan)

Reagents: HyClone™ DMEM/High Glucose Media (Thermo Scientific), Fetal Bovine Serum (FBS, Gibco®), HyClone® Phosphate Buffered Saline (PBS, Thermo Scientific), Antibiotic Antimycotic Solution (Pen/Strep/Fungizone 100×; Thermo Scientific), Trypan blue, 3-(4,5-dimethylthiazol-2-yl)-2,5-diphenyl tetrazolium bromide (MTT), and Dimethyl sulfoxide (DMSO, Sigma).

Equipment: Laminar Flow (VERTICAL HF-4BH).

Cell Culture: IMR-32 cells were cultured in DMEM/High Glucose Media (HyClone™) supplemented with 10% fetal bovine serum in 37° C., humidified air with 5% $CO_2$.

IMR-32 cells were seeded to 96-well plate at the density of $5\times10^4$ with 100 µL culture medium supplemented with 10% FBS for 24 hours. Upon dosing, the culture medium was changed to 100 µL medium supplemented with 5% FBS then, for each group, formulated to 25 mg/mL GMC1, 25 mg/mL GMA1, GMC1+0.3% GMA1 (GM) or PBS (control group) and 100 µL medium supplemented with 10% FBS (positive control group). Each group was repeated at least seven times in a 96-well plate and incubated for 72 hours for the MTT assay.

MTT assay: Removed culture dishes from incubator and transferred into laminar flow hood. Replaced the medium with 100 µL serum free medium with 0.5 mg/ml MTT reagent for each well and incubated for 30-60 minutes. Add equal volume of DMSO to each well and shake for 5 minutes. Measured the absorbance at 570 nm in an ELISA reader.

Data analysis and statistics: The results were analyzed with GraphPad Prism 6 and T-test was used for statistical analysis. The data shown was the percentage rate of cell viability±SEM.

Figure 13:
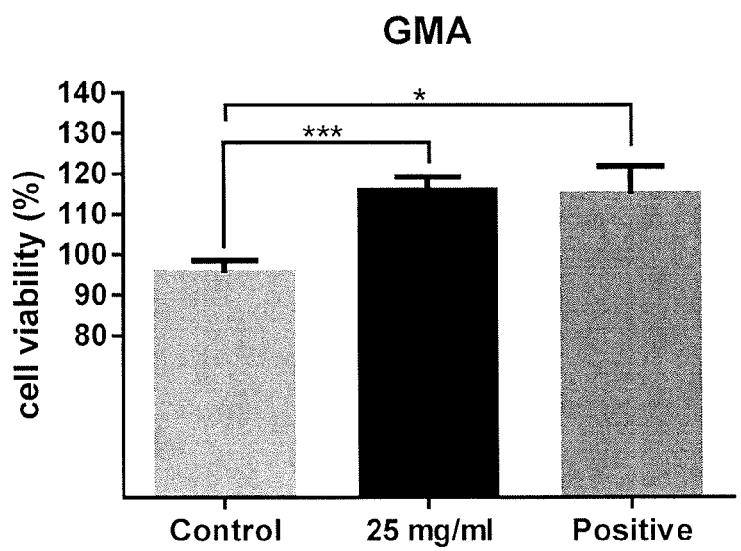
FIG. 13 shows the cell viability rates of IMR-32 cells treated with GMA1. The data are shown as the means±SEM of seven groups. The viability rates of IMR-32 cells treated with 25 mg/ml GMA and positive control are highly significantly and significantly increased (GMA1 p=0.0008, positive control p=0.0246). The results show that GMA1 promotes cell growth (*** $p<0.001$).
Figure 14:
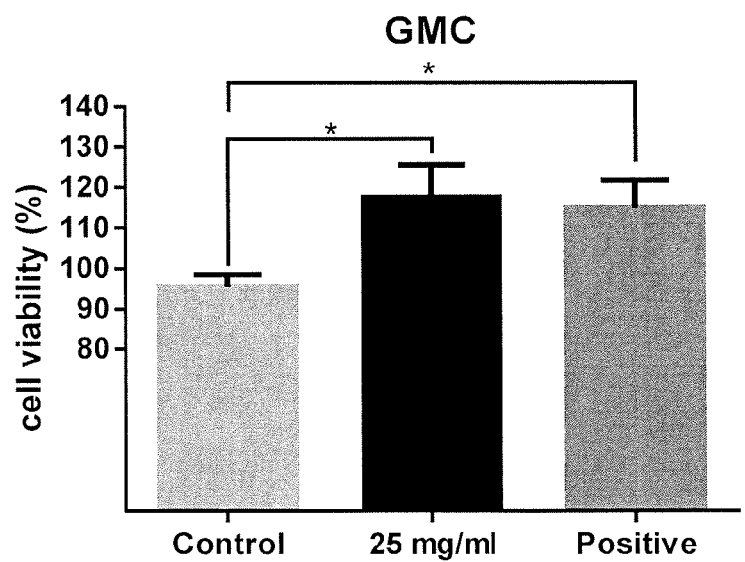
FIG. 14 shows the cell viability rates of IMR-32 cells treated with GMC1. The data are shown as the means±SEM of seven groups. The viability rates of IMR-32 treated with 25 mg/ml GMC1 and positive control are highly significantly and significantly increased (GMC1 p=0.0255 positive control p=0.0246). The results show that GMC1 promotes cell growth (* $p<0.05$).
Figure 15:
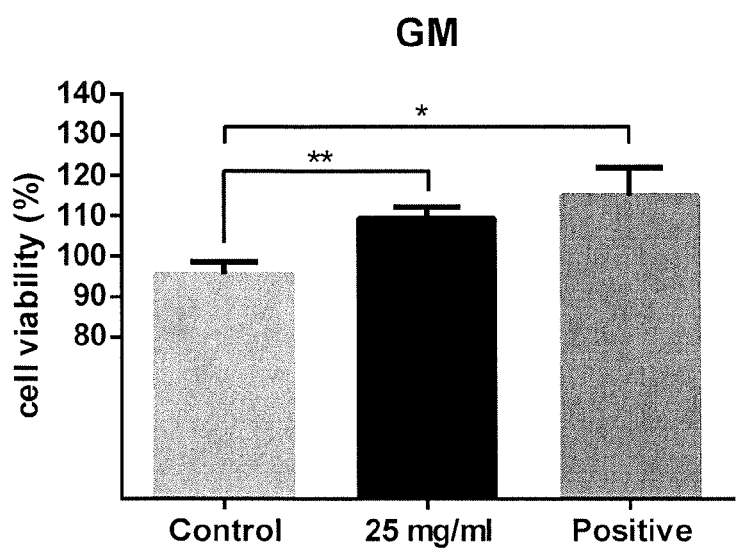
FIG. 15 shows the cell viability rates of IMR-32 cells treated with GMA1 and GMC1 (GM). The data are shown as the means±SEM of seven groups. The viability rate of IMR-32 cells treated with 25 mg/ml GM and positive control are highly significantly and significantly increased (GM p=0.0059, positive control p=0.0246). The results show that GM promotes cell growth (** $p<0.01$).

Results:

The cell viability rate is shown in Tables 7 to 9 and FIGS. 13 to 15. The cell viability rate is significantly increased after treated with 25 mg/mL GMA1 (Table 7 and FIG. 13), 25 mg/mL GMC1 (Table 8 and FIG. 14) or GMC1+0.3% GMA1 (GM, Table 9 and FIG. 15) compared to the PBS control group.

TABLE 7

| GMA1 Group | Control Mean ± SEM | 25 mg/mL Mean ± SEM | Positive Control Mean ± SEM |
| --- | --- | --- | --- |
| 1 | 99.2 ± 17.2 | 106.7 ± 8.3 | 137.9 ± 9.8 |
| 2 | 110.1 ± 6.9 | 119.7 ± 6.7 | 128.7 ± 13.8 |
| 3 | 86.3 ± 5.6 | 123.2 ± 6.3 ** | 94.5 ± 2.8 |
| 4 | 98.3 ± 1.8 | 130.2 ± 7.8 ** | 119.0 ± 7.7 * |
| 5 | 88.6 ± 2.6 | 114.2 ± 5.8 ** | 90.7 ± 1.6 |
| 6 | 94.8 ± 1.9 | 111.4 ± 6.1 * | 105.7 ± 3.1 * |
| 7 | 92.1 ± 5.7 | 105.7 ± 10.2 | 128.2 ± 2.9 *** |
| Average | 95.6 ± 3.0 | 115.9 ± 3.4 *** | 115.0 ± 6.9 * |

TABLE 8

| GMC1 Group | Control Mean ± SEM | 25 mg/mL Mean ± SEM | Positive Control Mean ± SEM |
| --- | --- | --- | --- |
| 1 | 99.2 ± 17.2 | 94.1 ± 3.3 | 137.9 ± 9.8 |
| 2 | 110.1 ± 6.9 | 144.1 ± 8.2 * | 128.7 ± 13.8 |
| 3 | 86.3 ± 5.6 | 120.0 ± 11.0 * | 94.5 ± 2.8 |
| 4 | 98.3 ± 1.8 | 149.2 ± 6.4 *** | 119.0 ± 7.7 * |
| 5 | 88.6 ± 2.6 | 106.4 ± 7.2 | 90.7 ± 1.6 |
| 6 | 94.8 ± 1.9 | 101.5 ± 3.1 | 105.7 ± 3.1 * |
| 7 | 92.1 ± 5.7 | 107.8 ± 6.3 | 128.2 ± 2 9 *** |
| Average | 95.6 ± 3.0 | 117.6 ± 8.1 * | 115.0 ± 6.9 * |

TABLE 9

| GM Group | Control Mean ± SEM | 25 mg/mL Mean ± SEM | Positive Control Mean ± SEM |
| --- | --- | --- | --- |
| 1 | 99.2 ± 17.2 | 117.2 ± 11.6 | 137.9 ± 9.8 |
| 2 | 110.1 ± 6.9 | 115.1 ± 12.5 | 128.7 ± 13.8 |
| 3 | 86.3 ± 5.6 | 103.0 ± 6.0 | 94.5 ± 2.8 |
| 4 | 98.3 ± 1.8 | 118.2 ± 10.1 | 119.0 ± 7.7 * |
| 5 | 88.6 ± 2.6 | 106.1 ± 5.5 * | 90.7 ± 1.6 |
| 6 | 94.8 ± 1.9 | 99.9 ± 2.0 | 105.7 ± 3.1 * |
| 7 | 92.1 ± 5.7 | 105.7 ± 1.6 * | 128.2 ± 2.9 *** |
| Average | 95.6 ± 3.0 | 109.3 ± 2.8 ** | 115.0 ± 6.9 * |

Remark of Tables 7 to 9: Each value represents the means±SEM. The comparison between different dosages of two groups was statistically analyzed using T-test. $p<0.05$ means there is a significant difference, and it is marked with *. $p<0.01$ means there is a highly significant difference, and it is marked with *. $p<0.001$ means there is a very highly significant difference, and it is marked with ***.

Extract Composition for Treating Brain Diseases and/or Neurodegenerative Diseases (I) Induced Dementia:

Material and Method:

Approximately 6 weeks old, with body weight rages of 250 g to 300 g male rats were obtained from BioLASCO, Taiwan. After 7 days of quarantine, rats were moved until the body weight over 300 g. The rats were identified by tail tattoos. Each cage tag was labeled with the cage number, study number, sex and group name. The rats were housed 2 per cage in polycarbonate cage in the animal facility.

The environment conditions were: temperature: 25±1° C.; humidity: 60±5%; light cycle: in light for 12 hours and in dark for 12 hours. Altromin 1324 FORTI (Germany) was supplied ad libitum throughout the study period. Tap water was supplied ad libitum via bottles attached to the cages.

The groups were shown in Table 10.

TABLE 10

| Groups | Dementia induction | Test article |
| --- | --- | --- |
| Normal | None | None |
| $AlCl_3$ | $AlCl_3$ | $AlCl_3$ control |
| $AlCl_3$ + cream base | $AlCl_3$ | Cream base |
| $AlCl_3$ + N2 | $AlCl_3$ | 0.5% GMA1 + GMC1 |

Dementia induction:

Eight weeks old rats were fed with daily oral administration of 15 mg/mL $AlCl_3$ solution at a dose of 100 mg/kg for 11 weeks to induce the mimic symptoms of dementia. The rats were divided into groups as shown in Table 10 and the test articles were topically applied to head and neck area with messaging for 30 seconds, and to nasal mucosa on week 5 to week 11. The training started on week 11 and the memory ability was then evaluated by a radial arm maze on week 11. The rats were continuously fed with $AlCl_3$ during the treatment.

Figure 16:
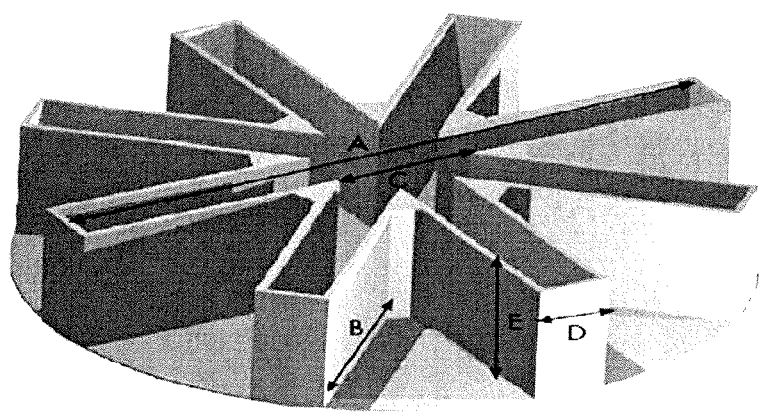
FIG. 16 shows the diagram of the radial arm maze.

Radial arm maze: Radial arm maze is one of the most common methods to measure spatial learning and memory in rats. The radial arm maze was designed by Olton in 70 s. It is based on forcing hungry rats to check food at the end of each arm, training them to remember locations of food in the maze in a period of time. This can measure the working memory (referring to short-term memory) and reference memory (referring to long-term memory) of rats at the same time. The radial arm maze is shown in FIG. 16. Size: (A) 122 cm; (B) 47 cm; (C) 30 cm; (D) 10 cm; (E) 20 cm.

The rats were habituated to the environment for 1 week. Weighed each rat and let rats fast for 24 hours. Prior to the experiment, kept the rats' body weight to be 80~85% of the original body weight; 60% of the normal diet was given after daily training (twice a day). On day 1 and day 2, the baits were scattered on the arms and central platform. Four rats were placed on the central platform at the same time and allowed to explore the maze for 10 minutes. On day 3 and 4, baits were placed on the end of each arm. Placed each rat separately on central platform and allow the rat to explore the maze until food finished. If the rat didn't finish all food within 10 minutes, training stopped. On day 5~14, baits were placed on the end of four fixed arms. Placed each rat on central platform and allowed to explore the maze until baits on four arms were finished. If the rat didn't finish all food within 10 minutes, training stopped. The arm entries were recorded and analyzed automatically. Each rat was trained twice each day, and there was one hour apart between two trainings.

The following three indicators were analyzed:
a. Working memory (short-term memory) errors (WME): number of reentries into baited arms.
b. Reference memory (long-term memory) errors (RME): number of reentries into unbaited arms.
c. Total memory errors (TME): WME+RME These three indicators stand for the abilities of learning and memory of rats, which would significantly increase along with the level of brain injuries.

Data analysis and statistics: The Student t-test and repeated ANOVA were used for statistical analysis. Data shown was mean results±SEM of each group. Data of $AlCl_3$ group was compared with normal group to calculate the statistical significance. Data of $AlCl_3$ group was also compared with $AlCl_3$+N2 group to calculate the statistical significance. If $p<0.05$, it is marked with *. If $p<0.01$, it is marked with **.

Figure 17:
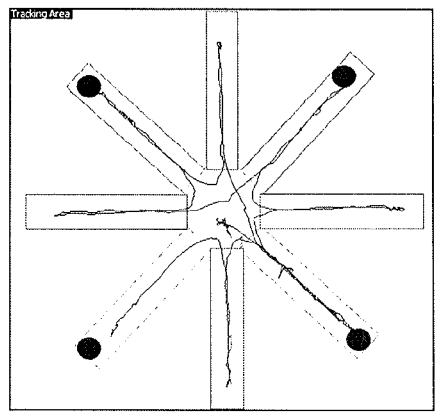
FIG. 17 shows the tracking paths of dementia rats in a radial arm maze. The tracking path of rats on Day 4 suggests that the rats in the $AlCl_3$+N2 group are able to reach locations of baits with their memory after training, and the rats in the $AlCl_3$ group and $AlCl_3$+cream base group are not.
Figure 17:
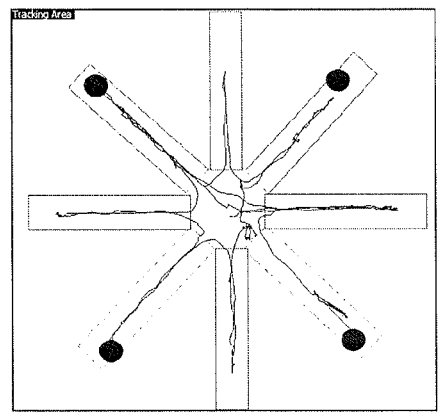
Figure 17:
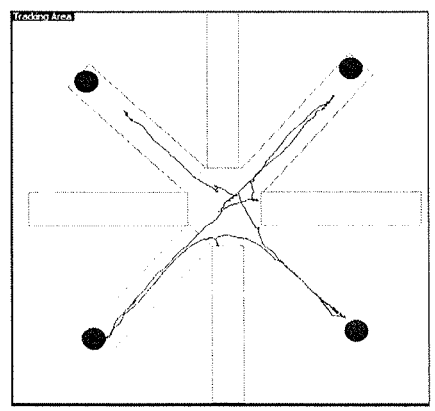
Figure 18:
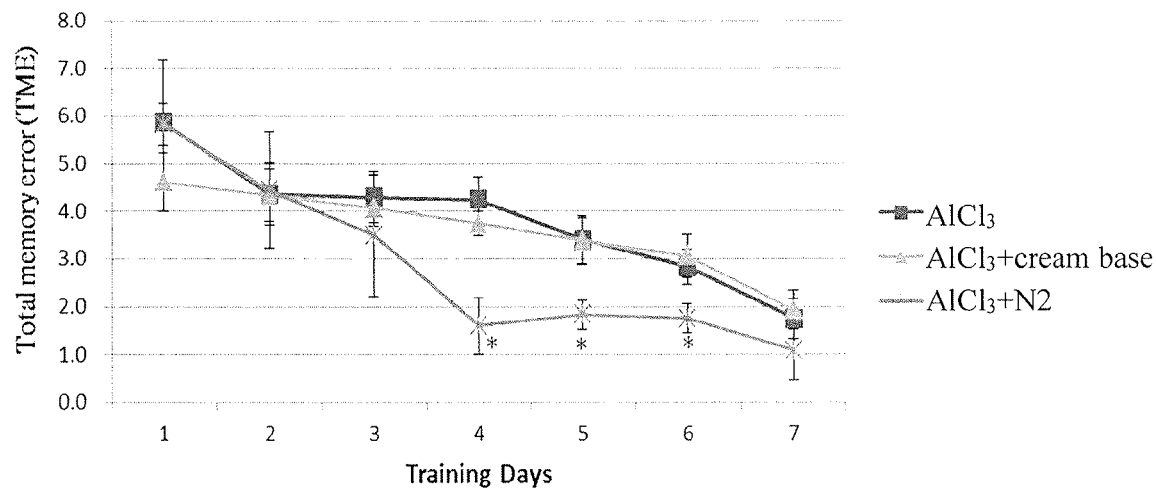
FIG. 18 shows the diagram of the total number of errors (TME) of dementia rats in the radial arm maze test. The TME values of $AlCl_3$ group and $AlCl_3$+cream base group show no significant difference ($p>0.05$), and the TME values on Day 4 after the treatment of the extract composition comprising the soybean seed extract and soybean seed vapor fraction are significantly lower than those of $AlCl_3$ group ($AlCl_3$+N2 p=0.0128). It shows that the extract composition comprising the soybean seed extract and soybean seed vapor fraction has the effect on treating dementia in rats. The data are shown as means±SEM. The Student t-test and repeated ANOVA are used for statistical analysis. When comparing $AlCl_3$ group and $AlCl_3$+cream base group, $p<0.05$ is marked with *, and $p<0.01$ is marked with **, meaning that there is a significant difference in statistics.
Figure 19:
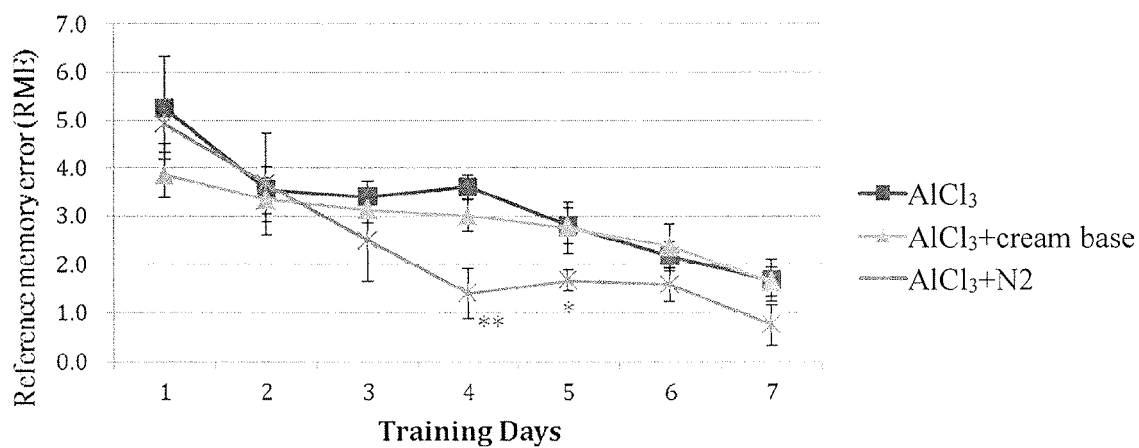
FIG. 19 shows the diagram of the reference (long-term) memory errors (RME) of dementia rats in the radial arm maze test. The RME values of $AlCl_3$ group and $AlCl_3$+cream base group show no significant difference (p>0.05), and the RME values on Day 4 after the treatment of the extract composition comprising the soybean seed extract and soybean seed vapor fraction are significantly lower than those of $AlCl_3$ group (p=0.0046). It shows that the extract composition comprising the soybean seed extract and soybean seed vapor fraction has the effect on restoring the long-term memory of rats. The data are shown as means±SEM. The Student t-test and repeated ANOVA are used for statistical analysis. $p<0.05$ is marked with *, and $p<0.01$ is marked with **, meaning that there is a significant difference in statistics.
Figure 20:
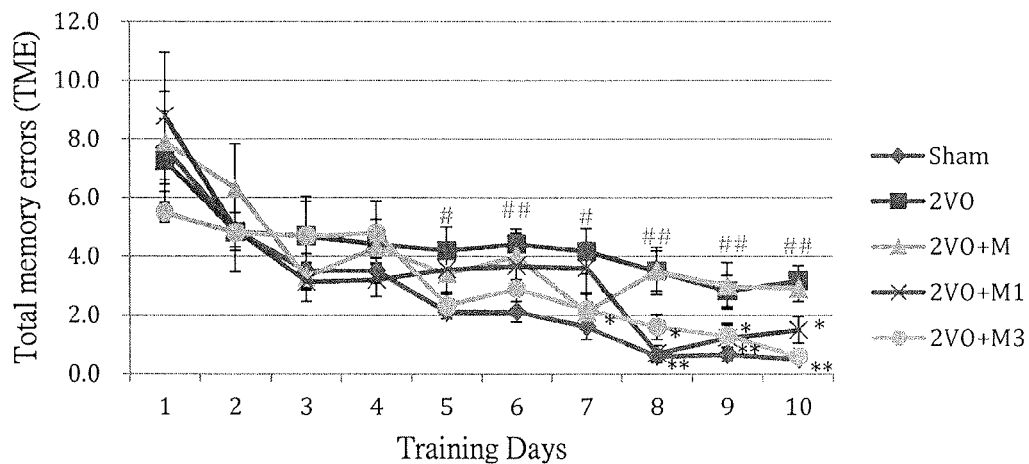
FIG. 20 shows the diagram of the total number of errors (TME) of vascular dementia rats treated with cream base (M), GMC1(M1), and GMC1+0.5% GMA1 (M3) in the radial arm maze test. It shows the TME of two-sided carotid arterial ligature (2VO) group is significantly higher than Sham group (day 8, p=0.0013), which refers to successful induction of vascular dementia in rats by two-sided carotid arterial ligature. The results show that TME values are significantly improved compared with 2VO group after treated by M1 and M3 (day 8, M1 p=0.0019; M3 p=0.0355). This suggests that M1 and M3 have efficacy for treating vascular dementia in rats. The data are shown as means±SEM. The Student t-test and repeated ANOVA are used for statistical analysis. $p<0.05$ is marked with *, and $p<0.01$ is marked with **, meaning that there is a significant difference in statistics.
Figure 21:
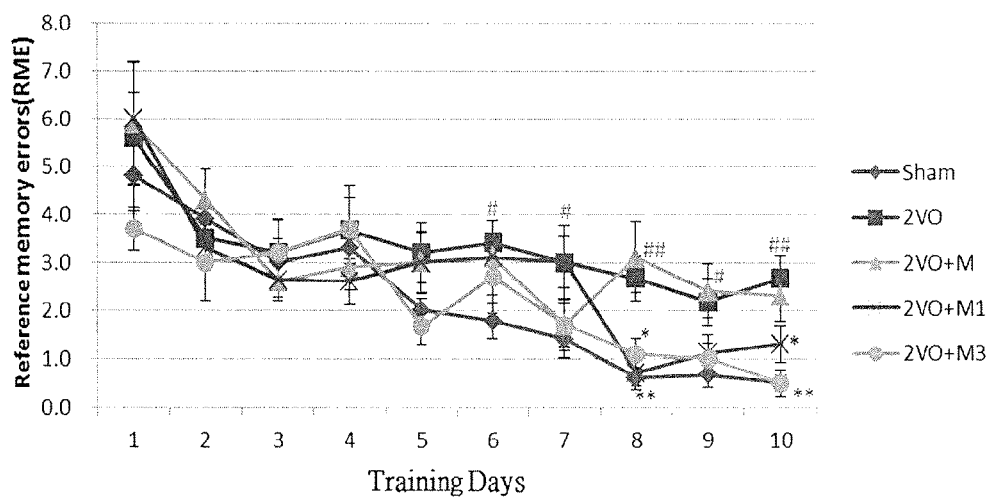
FIG. 21 shows the diagram of the reference (long-term) memory errors (RME) of vascular dementia rats treated with cream base (M), GMC1(M1), and GMC1+0.5% GMA1 (M3) in the radial arm maze test. It shows that the RME of two-sided carotid arterial ligature (2VO) group is significantly higher than Sham group (day 8, p=0.0016), which refers to successful induction of vascular dementia in rats by two-sided carotid arterial ligature. The results show that RME values are significantly improved compared to 2VO group after treated by M1 and M3 (day 8, M1 p=0.0029; M3 p=0.0171). This suggests that M1 and M3 have efficacy for treating RME of vascular dementia in rats. The data are shown as means±SEM. The Student t-test and repeated ANOVA are used for statistical analysis. $p<0.05$ is marked with *, and $p<0.01$ is marked with**, meaning that there is a significant difference in statistics.
Figure 22:
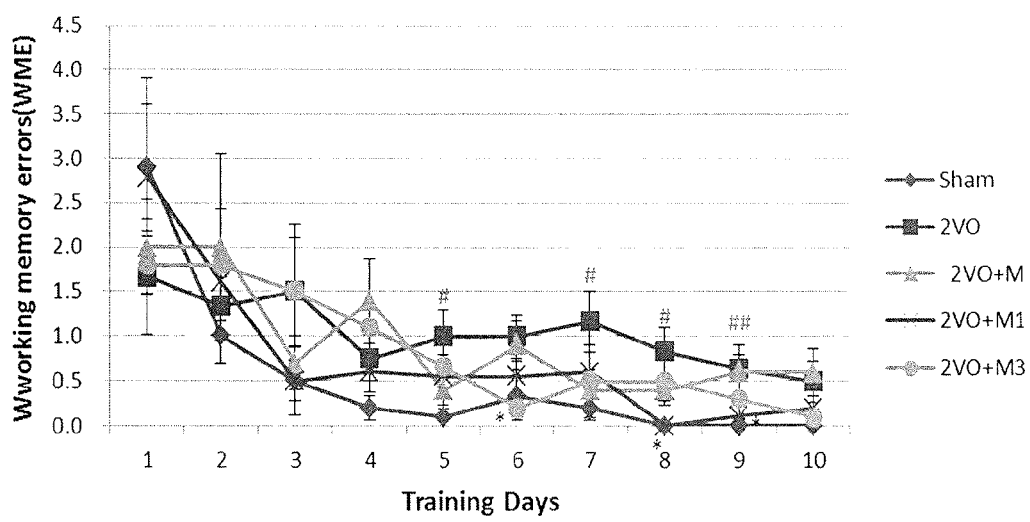
FIG. 22 shows the diagram of the working memory (short-term memory) errors (WME) of vascular dementia rats treated with cream base (M), GMC1(M1), and GMC1+0.5% GMA1 (M3) in the radial arm maze test. It shows that the WME of two-sided carotid arterial ligature (2VO) group is significantly higher than Sham group (day 8, p=0.0111), which refers to successful induction of vascular dementia in rats by two-sided carotid arterial ligature. The results show that WME values are significantly improved compared to 2VO group after treated by M1 and M3 (day8, M1 p=0.0111; M3 p=0.0139). This suggests that M and M3 have efficacy for treating WME vascular dementia in rats. The data are shown as means±SEM. The Student t-test and repeated ANOVA are used for statistical analysis. $p<0.05$ is marked with *, and $p<0.01$ is marked with**, meaning that there is a significant difference in statistics.
Figure 23:
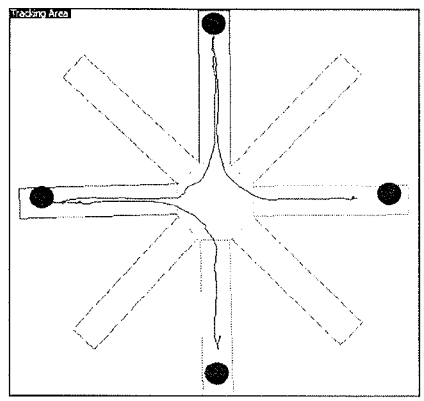
FIG. 23 shows the tracking path of vascular dementia (VD) rats in a radial arm maze. The tracking path of VD rats on day 8 suggests that sham group, GMC1 (M1) and GMC1+0.5% GMA1 (M3) groups are able to reach the locations of baits with their memory after training, while 2VO and M groups are not.
Figure 23:
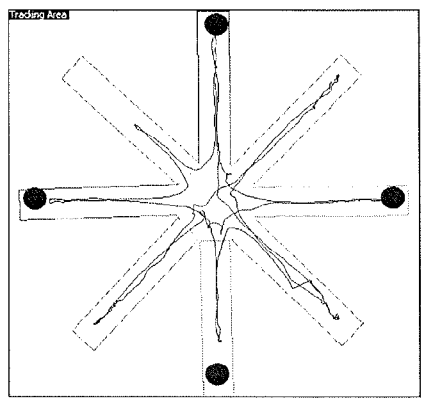
Figure 23:
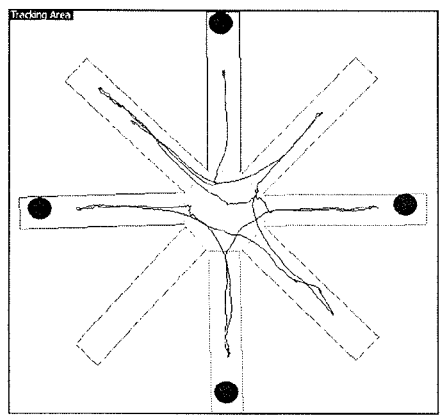
Figure 23:
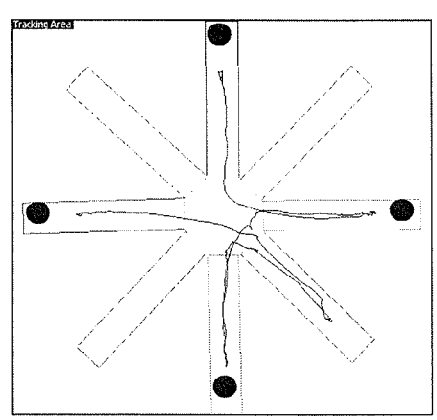
Figure 23:
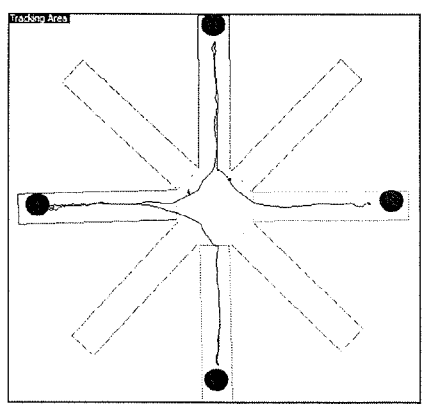
Figure 24:
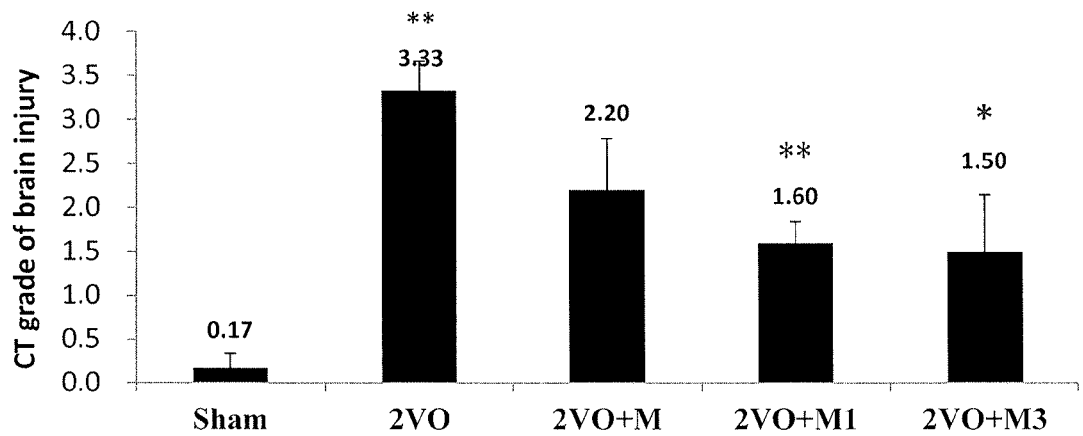
FIG. 24 shows the statistical diagram of brain injury grades of vascular dementia rats. The extent of brain injury in accordance with CT images of rat brain is classified to grade 0~4. The results suggest that severe brain injuries of 2VO (p=0.0000) group is significantly reduced with GMC1 (M1) and GMC1+0.5% GMA1 (M3) treatments (M1 p=0.0030; M3 p=0.0238). The data are shown as means±SEM. The Student t-test and repeated ANOVA are used for statistical analysis. $p<0.05$ is marked with *, and $p<0.01$ is marked with **, meaning that there is a significant difference in statistics.

Results:

It has been reported that heavy metal-induced dementia is similar to Alzheimer's disease. Both of them induce the formation of amyloid precursor proteins, and the results in the formation of senile plaques and neurofibrillary tangles. Therefore, we employed the heavy metal-induced dementia rat as the animal model to understand the effect of the extract composition containing the soybean seed extract and soybean seed vapor fraction on Alzheimer's—like diseases. The results are shown in FIGS. 17 to 19. Referring to FIG. 17, the tracking path of rats on Day 4 suggests that the rats of the $AlCl_3$+N2 group are able to reach the locations of baits with their memory after training, and the rats of the $AlCl_3$ group and $AlCl_3$+cream base group are not. Referring to FIG. 18, the TME values of $AlCl_3$ group and $AlCl_3$+cream base group show no significant difference ($p>0.05$), and the TME values on Day 4 after the treatment of the extract composition comprising the soybean seed extract and soybean seed vapor fraction are significantly lower than those of $AlCl_3$ group ($AlCl_3$+N2 $p=0.0128$). It shows that the extract composition comprising the soybean seed extract and soybean seed vapor fraction has the effect on treating dementia rats. Referring to FIG. 19, the RME values of $AlCl_3$ group and $AlCl_3$+cream base group show no significant difference ($p>0.05$), and the RME values on Day 4 after the treatment of the extract composition comprising the soybean seed extract and soybean seed vapor fraction are significantly lower than those of $AlCl_3$ group ($p=0.0046$). It shows that the extract composition comprising the soybean seed extract and soybean seed vapor fraction has the effect on restoring the long-term memory of rats. The results show that the errors of $AlCl_3$ group are significantly higher than the control group in the radial arm maze test, which refers to successful induction of dementia by $AlCl_3$ in rat. The memory impairment of reference memory is also significantly improved after treated by the extract composition comprising the soybean seed extract and soybean seed vapor fraction. This indicates that the extract composition comprising the soybean seed extract and soybean seed vapor fraction has the efficacy in treating dementia.

(II) Vascular Dementia:

Material and Method:

The groups were shown in Table 11.

TABLE 11

| Groups | Dementia induction | Test article |
| --- | --- | --- |
| Sham | none | sham |
| 2VO | two-sided carotid arterial ligature | two-sided carotid arterial ligature control group |
| M | two-sided carotid arterial ligature | Cream base |
| M1 | two-sided carotid arterial ligature | GMC1 |
| M3 | two-sided carotid arterial ligature | GMC1 + 0.5% GMA1 |

Rats and animal facility are as described in (I) induced dementia.

Rats were anesthetized with 1:1.5 ketamine-Rompun mixtures (0.1 mL/100 g, i.p.) and were fixed on the surgery plate. Both common carotid arteries were exposed via a midline cervical incision in the dorsal neck region and were double-ligated with silk sutures. The wounds were sutured and the rats were placed under warm light until they recovered.

The cream base (M), GMC1(M1), and GMC1+0.5% GMA1 (M3) were topically applied (2 g/rat) to head and neck area with massaging for 30 seconds, and to nasal mucosa. Treatment continued for four weeks, and memory of rats was measured by radial arm maze in the last two weeks. The radial arm maze test is as described in (I) induced dementia.

Data analysis and statistics: The unpaired Student t-test and two-way ANOVA were used for statistical analysis. Data shown was mean results±SEM of each group. Data of Sham group was compared with 2VO group to calculate the statistical significance. Drug treated groups was compared with 2VO group to calculate the statistical significance. $p<0.05$ means there is a significant difference, and it is marked with *. $p<0.01$ means there is a very significant difference, and it is marked with **.

Results:

The number of errors of 2VO group is significantly higher than Sham group (FIGS. 20 to 23), which refers to successful induction of vascular dementia in rats by two-sided carotid arterial ligature, and the memory impairment caused by vascular dementia is significantly improved after two weeks of M1 and M3 treatments. According to the results of Computed Tomography scan of the VD rat brains, bilateral occlusion of both common carotids arteries (2VO) caused swelling, softening, histolysis of brain tissues, or even blood clot formation, and thus induced the dementia. The brain injuries are significantly decreased after M1 and M3 treatments.

Extract Composition for Treating Breast Cancer and Reducing Side Effects of Interfering with DNA and/or RNA Replication Drugs, and/or Enhancing Pharmaceutical Effects of Interfering with DNA and/or RNA Replication Drugs Material:

Cell line and reagent: MDA-MB-231 (purchased from Food Industry Research and Development Institute, Taiwan); Penicillin-Streptomycin-Neomycin Mixture (100×), fetal bovine serum (FBS) and Dulbecco's Modified Eagle Medium (DMEM) were purchased from Gibco®; cyclophosphamide (CTX, Endoxan®).

Animal facility: Approximately 6 to 8 week-old BALB/cAnN.Cg-Foxn1$^{nu}$/Cr1Nar1 female mice were obtained from National Laboratory Animal Center, Taiwan. The environment conditions were: temperature: 25±1° C.; humidity: 60±5%; independent air condition; controlled light cycle. Water and food was supplied ad libitum throughout the study period. The mice were housed according to the standard procedure of the laboratory animal committee.

Tumor-bearing mice induction: MDA-MB-231 cells (human breast cancer cells) were cultured until 5×10$^6$ cells, the cells required in injection of female nude mice were collected with trypsin, and resuspended in PBS solution for tumor induction. The tumor of nude mice was induced by subcutaneous injected with 100 μL of cell solution and released back into the cages to be a normal diet. When the tumor was about 300 mm$^3$, the mice were subjected to topical administration of different doses of the extract composition and grouping into CTX group and non-CTX group. The weight, appetite, blood sugar and tumor size growth were observed every week to assess the appearance of the normal physiological state of nude mice to understand the efficacy of the extract composition.

Grouping the tumor-bearing mice and treatment: When the tumor was about 300 mm$^3$, the mice were subjected to grouping as shown in Table 12. The chemotherapy drug (an injection a week) was administrated with the extract composition. The treating group was topically applied to the tumor area, skin around the tumor, and the whole back skin with the dosage of 0.1 g/day. After treatment for 5 weeks, the weight, appetite, blood sugar and tumor size growth of the nude mice were observed.

TABLE 12

| Group | Tumor induction | Chemotherapy drag | Test article |
| --- | --- | --- | --- |
| Normal | None | None | None |
| Tumor | MDA-MB-231 induction | None | None |
| J1 | MDA-MB-231 induction | None | GMC1 |
| J2 | MDA-MB-231 induction | None | 0.3% GMA1 |
| NO CTX + L5 | MDA-MB-231 induction | None | GMC1 + 0.5% GMA1 |
| CTX | MDA-MB-231 induction | CTX/4 injections | None |
| CTX + L1 | MDA-MB-231 induction | CTX/4 injections | Cream base |
| CTX + L5 | MDA-MB-231 induction | CTX/4 injections | GMC1 + 0.5% GMA1 |

Clinical assessment of tumor-bearing mice: The physiological state and tumor size of the tumor-bearing mice were assessed including weight, appetite, blood sugar and tumor size. The tumor size was calculated according to: tumor volume (mm$^3$)=ab$^2$/2, to assess the tumor growth rate.

Results:

In the model of tumor-bearing nude mice induced by human breast cancer cell MDA-MB-231, after the treatment, the extract compositions J1 and J2 show effect on inhibiting tumor growth in nude mice (Table 13 and FIG. 25). In the physiological state assessment, the extract composition groups show better appetite and blood sugar value.

TABLE 13

| | Tumor size (mm$^3$) | | | |
| --- | --- | --- | --- | --- |
| | Week 0 | Week 1 | Week 2 | Week 3 |
| J1 | 0.0 | 63.40 | 126.23 | 369.51 |
| J2 | 0.0 | −2.02 | 26.83 | 182.19 |
| Tumor | 0.00 | 72.69 | 380.71 | 696.90 |

In GMC1+0.5% GMA1 (NO CTX+L5) group, it shows that the extract composition inhibits the tumor growth in nude mice (FIG. 26).

Compared to the normal group, the physiological state and tumor growth of the tumor+chemotherapy drug group (CTX group), extract composition+chemotherapy drug group (CTX+L1 and CTX+L5 groups) was assessed. Referring to Table 14 and FIGS. 26 and 27, the results of CTX+L1 and CTX+L5 groups show enhancing effect of the chemotherapy drug on eliminating tumor in the tumor-bearing mice administrated with the chemotherapy drug without affecting the body weight, the average food intake and the average blood sugar (Tables 15 to 17).

TABLE 14

| | tumor size elimination (mm$^3$) | | | | | | | | | |
| --- | --- | --- | --- | --- | --- | --- | --- | --- | --- | --- |
| | 4/28 | 5/2 | 5/5 | 5/9 | 5/12 | 5/16 | 5/19 | 5/23 | 5/26 | 5/30 |
| Normal | 0.00 | 0.00 | 0.00 | 0.00 | 0.00 | 0.00 | 0.00 | 0.00 | 0.00 | 0.00 |
| Tumor | 0.00 | 108.05 | 364.31 | 428.36 | 627.45 | 874.62 | 1295.63 | 1961.51 | 2727.56 | 2938.30 |
| CTX | 0.00 | 99.61 | 78.95 | −19.52 | −45.11 | −157.57 | −176.41 | −264.85 | −293.68 | −391.42 |
| CTX + L1 | 0.00 | 89.22 | 113.36 | 21.27 | −46.75 | −138.97 | −179.55 | −224.38 | −294.03 | −384.43 |
| CTX + L5 | 0.00 | 149.85 | 173.28 | 48.54 | −56.91 | −170.01 | −220.34 | −274.15 | −338.79 | −510.04 |

TABLE 15

| average body weight (g) | | | | | | | | | | |
|---|---|---|---|---|---|---|---|---|---|---|
| | 4/28 | 5/2 | 5/5 | 5/9 | 5/12 | 5/16 | 5/19 | 5/23 | 5/26 | 5/30 |
| Normal | 20.61 | 21.34 | 20.91 | 21.16 | 20.31 | 21.13 | 20.41 | 21.90 | 21.63 | 21.96 |
| Tumor | 19.64 | 19.11 | 20.03 | 18.75 | 18.57 | 20.22 | 20.48 | 21.36 | 21.74 | 22.67 |
| CTX | 19.64 | 20.04 | 18.46 | 19.00 | 19.51 | 20.99 | 20.42 | 21.16 | 20.21 | 22.18 |
| CTX + L1 | 20.05 | 20.59 | 18.72 | 19.34 | 18.79 | 19.23 | 19.98 | 20.08 | 19.94 | 21.31 |
| CTX + L5 | 19.12 | 19.51 | 18.45 | 19.09 | 19.23 | 19.61 | 19.93 | 19.69 | 19.03 | 20.52 |

TABLE 16

| average food intake (g) | | | | | | | |
|---|---|---|---|---|---|---|---|
| | 5/5~5/9 | 5/9~5/12 | 5/12~5/16 | 5/16~5/19 | 5/19~5/23 | 5/23~5/26 | 5/26~5/30 |
| Normal | 4.95 | 4.75 | 5.18 | 4.69 | 4.52 | 4.37 | 4.50 |
| Tumor | 4.94 | 4.48 | 4.56 | 4.75 | 4.25 | 4.65 | 4.20 |
| CTX | 4.89 | 5.61 | 5.38 | 5.21 | 4.70 | 4.76 | 5.22 |
| CTX + L1 | 4.45 | 4.58 | 4.88 | 4.64 | 4.08 | 4.01 | 4.46 |
| CTX + L5 | 4.60 | 5.12 | 4.47 | 5.09 | 4.36 | 4.21 | 4.62 |

TABLE 17

| average blood sugar (dL) | | | | | |
|---|---|---|---|---|---|
| | 5/2 | 5/9 | 5/16 | 5/23 | 5/30 |
| Normal | 110 | 84 | 99 | 97 | 98 |
| Tumor | 60 | 66 | 82 | 89 | 74 |
| CTX | 113 | 93 | 109 | 122 | 108 |
| CTX + L1 | 110 | 93 | 92 | 99 | 101 |
| CTX + L5 | 110 | 109 | 104 | 106 | 102 |

Clinically, one of the main reasons for abandonment of cancer treatment is cancer pain caused by cancer. It is found that cancer pain is caused in part by the tumor, mainly due to the inflammation and nerve compression caused by tumor invasion to the internal organs, peripheral nerves, and bones. The extract composition can effectively inhibit tumor growth, and also suppress cancer pain caused by cancer in part, and is helpful in the treatment.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for promoting neuron cell proliferation and/or treating brain diseases and/or neurodegenerative diseases in a subject in need of such promotion and/or treatment comprising administering to said subject an effective amount of an extract composition comprising a soybean seed extract, which soybean seed extract is prepared by a process comprising steps of:
  (a) providing soybean seeds and an extracting solution, which extracting solution is water or an alcohol solution containing alcohol at the concentration lower than about 90 wt %;
  (b) extracting the soybean seeds with the extracting solution at a barometric pressure lower than about 1 atm and at a temperature lower than about 60° C. to obtain an crude extract; and
  (c) removing solids from the crude extract to obtain a liquid portion;
  wherein the soybean seeds are seeds from yellow soybean or black soybean, and
  wherein the brain diseases and/or neurodegenerative diseases are selected from the group consisting of vascular dementia, Alzheimer's disease, Parkinson's disease, cerebral vascular disease, inflammatory brain injury, brain damage surrounding inflammatory response, brain lesions, cerebral hematoma, swelling ventricle and ventricular dilatation.

2. The method according to claim 1, wherein the neuron cell is a neuroblastoma cell.

3. The method according to claim 1, wherein the extract composition is formulated as a skin or mucosal topical agent.

4. The method according to claim 1, wherein the process for preparing the soybean seed extract further comprises a step (d) of concentrating the liquid portion obtained in the step (c) to obtain a concentrated solid portion.

5. The method according to claim 4, wherein the process for preparing the soybean seed extract further comprises a step (e) of drying the concentrated solid portion obtained in the step (d).

6. The method according to claim 1, wherein the extract composition further comprises a soybean seed vapor fraction, which soybean seed vapor fraction is prepared by a process comprising steps of:
  (i) providing soybean seeds in a second extracting solution, which second extracting solution is water or an alcohol solution containing alcohol at the concentration lower than about 15 wt %; and
  (ii) extracting the soybean seeds with the second extracting solution at a barometric pressure lower than about 1 atm and at a temperature lower than about 110° C. and collecting the vapor fraction.

7. The method according to claim 6, wherein the alcohol solution in step (i) contains alcohol at the concentration lower than about 5 wt %.

8. The method according to claim 6, wherein the content of the soybean seed extract is from about 0.001 wt % to about 5 wt %; and the content of the soybean seed vapor fraction is from about 95 wt % to about 99.999 wt %.

9. The method according to claim 1, wherein the extract composition consists essentially of the soybean seed extract and the soybean seed extract is prepared by a process consisting essentially of steps (a), (b) and (c).

* * * * *